United States Patent [19]
Ahmed

[11] Patent Number: 5,681,275
[45] Date of Patent: Oct. 28, 1997

[54] OPHTHALMOLOGICAL DEVICE WITH ADAPTABLE MULTIPLE DISTRIBUTION PLATES

[76] Inventor: Abdul Mateen Ahmed, 928 E. Juanita Ave., La Verne, Calif. 91750

[21] Appl. No.: 592,466

[22] Filed: Jan. 26, 1996

Related U.S. Application Data

[63] Continuation-in-part of Ser. No. 269,839, Jul. 1, 1994, Pat. No. 5,616,118, which is a continuation-in-part of Ser. No. 786,734, Oct. 1, 1991, Pat. No. 5,411,473, which is a division of Ser. No. 478,655, Feb. 12, 1990, Pat. No. 5,071,408, which is a continuation-in-part of Ser. No. 255,070, Oct. 7, 1988, abandoned.

[51] Int. Cl.⁶ ................................................. A61M 5/00
[52] U.S. Cl. ...................................... 604/9; 604/8
[58] Field of Search ...................... 604/8, 9, 10, 185; 137/510

[56] References Cited

U.S. PATENT DOCUMENTS

| | | |
|---|---|---|
| 3,288,142 | 11/1966 | Hakim ............................ 604/9 |
| 4,332,255 | 6/1982 | Hakim et al. .................... 604/175 |
| 4,387,715 | 6/1983 | Hakim et al. .................... 604/9 |
| 4,560,375 | 12/1985 | Schulte et al. .................. 604/8 X |
| 4,588,394 | 5/1986 | Schulte et al. .................. 604/8 X |
| 4,729,761 | 3/1988 | White ........................... 604/8 |
| 4,741,730 | 5/1988 | Dormandy, Jr. et al. ........... 604/8 |
| 4,850,955 | 7/1989 | Newkirk ......................... 604/9 |
| 5,069,663 | 12/1991 | Sussman ......................... 604/9 |

Primary Examiner—Sam Rimell
Attorney, Agent, or Firm—John J. Connors; Connors & Assoc.

[57] ABSTRACT

A medical device includes a one-way flow valve in communication with fluid to be drained. The valve is connected to a primary distribution plate which has a raised perimeter with at least one opening in the perimeter. There is a secondary distribution plate having a raised perimeter with at least one opening in the perimeter. At least one pair of plugs, each having a central passageway, are inserted into the openings in the perimeters of the primary and secondary distribution plates, and an connecting tube places the primary and secondary distribution plates in fluid communication with each other. The tube is sized to fit inside the central passageway of the plugs, with the connecting tube having opposed ends, each end inserted to the passageway in the plugs. The distance between the plugs is adjusted by sliding the plugs along the length of the connecting tube.

16 Claims, 17 Drawing Sheets

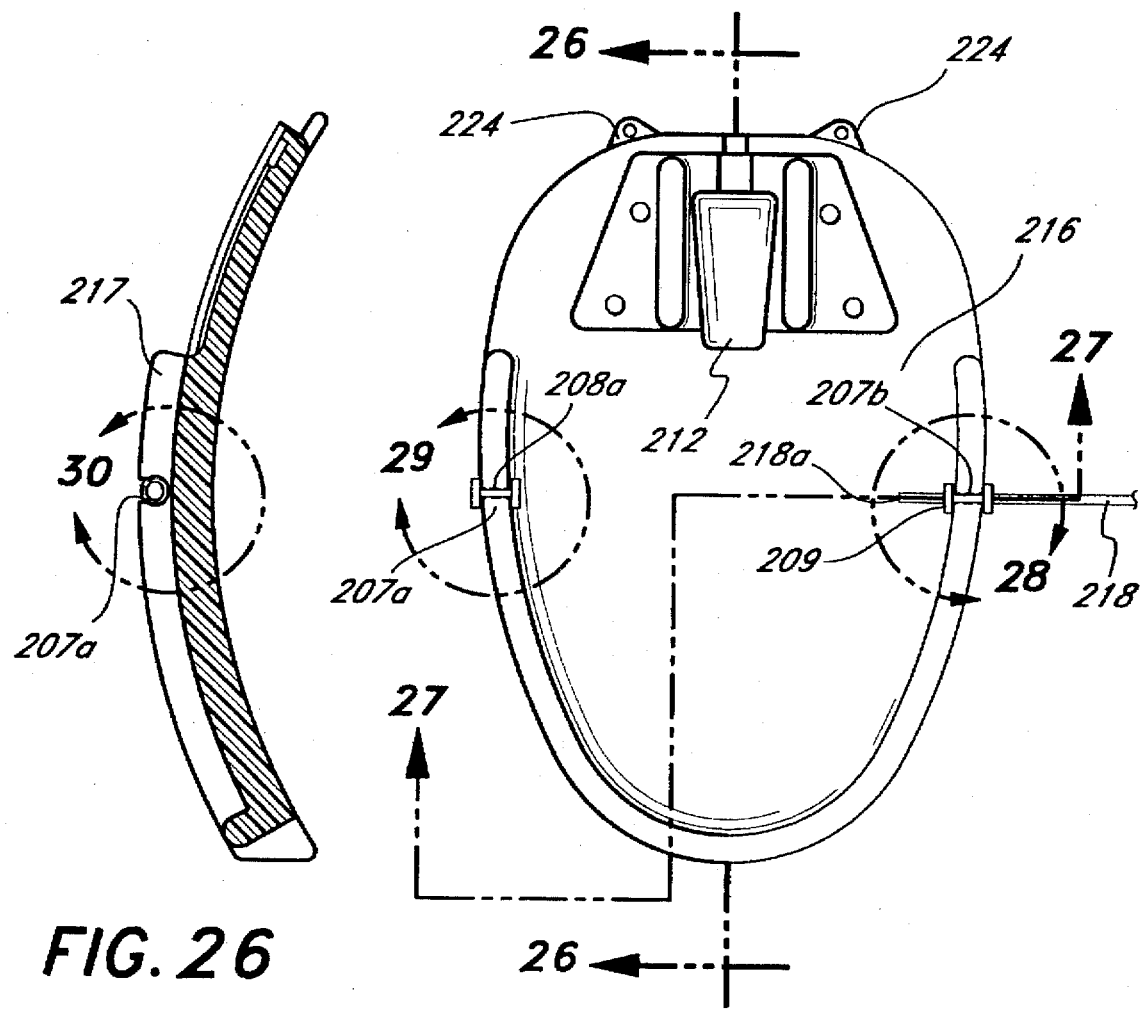

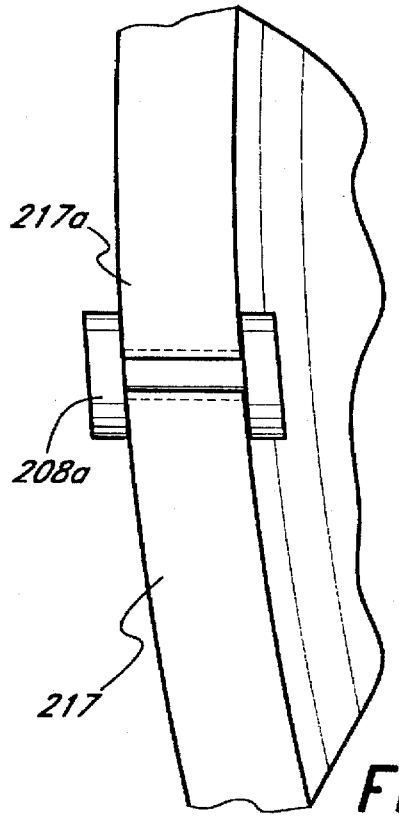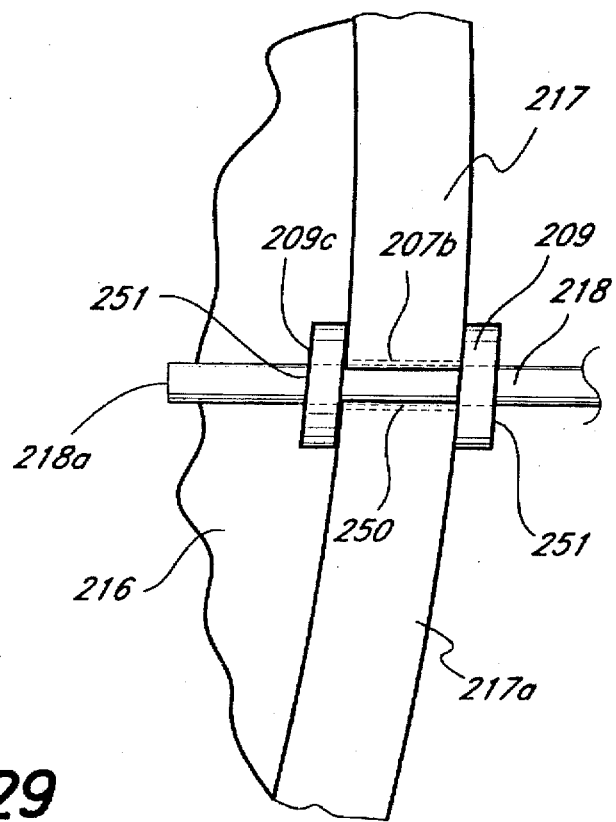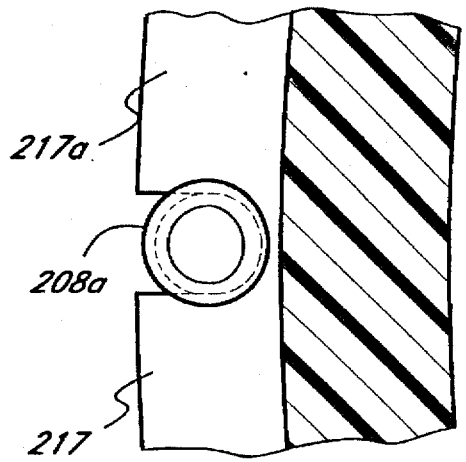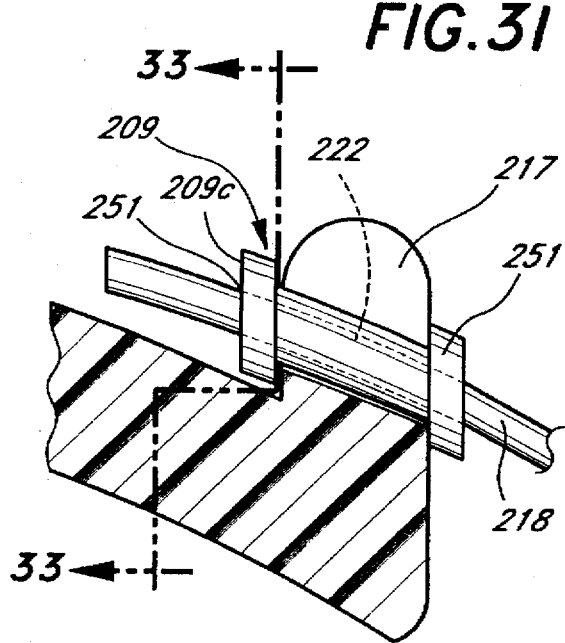

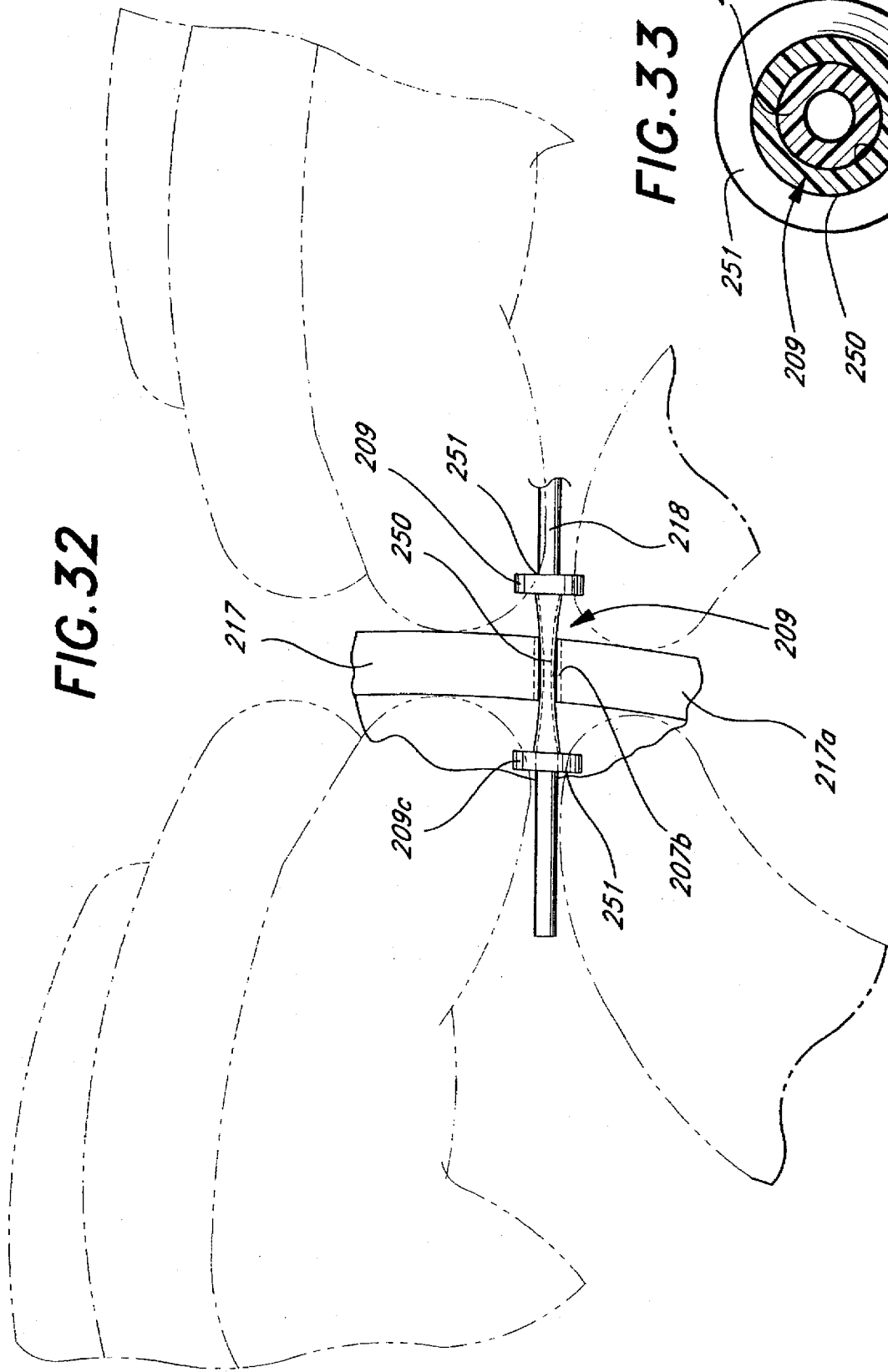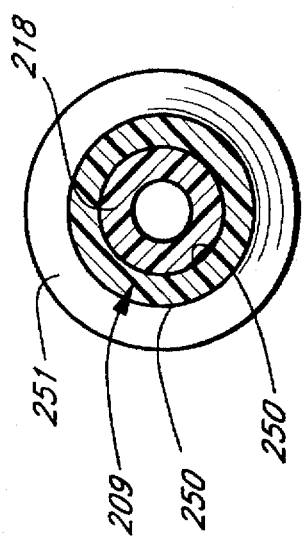

OPHTHALMOLOGICAL DEVICE WITH ADAPTABLE MULTIPLE DISTRIBUTION PLATES

RELATED PATENT APPLICATIONS

This application is a continuation-in-part application of U.S. Ser. No. 08/269,839, entitled "Uniquely Shaped Ophthalmological Device," filed Jul. 1, 1994, now U.S. Pat. No. 5,616,118, which is a continuation-in-part application of U.S. Ser. No. 07/786,734, entitled "Medical Valve," filed Oct. 1, 1991, now U.S. Pat. No. 5,411,473, which is a divisional application of U.S. Ser. No. 07/478,655, filed Feb. 12, 1990, and entitled "Medical Valve," now U.S. Pat. No. 5,071,408, which is continuation-in-part application of U.S. patent application Ser. No. 07/255,070, entitled "Self-Regulating Pressure Control Glaucoma Valve" filed Oct. 7, 1988, now abandoned. All of these related applications are incorporated herein by reference and made a part of this application.

FIELD OF THE INVENTION

This invention relates to medical devices which are implanted in the human body, particular to an ophthalmological device which is easy to manufacture, performs reliably, is easy to surgically implant in the human body, and will remain functional for the time required by the patient in which it is implanted.

BACKGROUND DISCUSSION

Medical valves are used for many different types of applications. One such application is to treat glaucoma by allowing aqueous humor to drain from the intraocular chamber of the eye to relieve excess pressure.

Thomas C. White in U.S. Pat. No. 4,554,918 has suggested one type of glaucoma valve where the aqueous humor flows from the intraocular chamber through a tube into an external reservoir. The end of the tube in communication with the reservoir has a small opening in its end. The small opening provides a great deal of resistance to flow of the aqueous humor which is highly viscous. The White valve provides for flow in only one direction, namely, from the intraocular chamber of the eye to the external reservoir. Upon being filled, the reservoir is pressed by the patient to force the aqueous humor contained in the reservoir through another tube into the body of the patient where it is absorbed.

Another device used to treat glaucoma is discussed by Anthony C. B. Molteno in U.S. Pat. No. 4,750,901. This device includes a plate having a tube that extends into the intraocular chamber. The aqueous humor from the intraocular chamber flows onto the surface of the plate and is absorbed by the body. A third device to treat glaucoma is discussed by Molteno in U.S. Pat. No. 4,457,757. This device has two fluid collection plates together inflexible and rigidly fixed together.

All these devices have been used to treat glaucoma, but the White valve suffers from the disadvantage that the patient must manually press the reservoir in order to force the aqueous humor collected in the reservoir to escaped and be absorbed by the body. Moreover, although the White valve is designed to open when the intraocular pressure becomes excessive, the valve's structure is not reliable, because it depends upon a tiny diameter and can easily be clogged by particulates. In addition, the White valve is very insensitive, failing to respond to slight changes in pressure to open and close.

The Molteno plate overcomes the objections of the manually actuated reservoir, however, it does not employ a valve and could lead to hypotony, that is, the loss of aqueous humor within the intraocular chamber of the eye. The device discussed by Molteno in U.S. Pat. No. 4,457,757, in addition to the lack of a pressure controlling assembly, further limits the ophthalmologist to one fixed length and configuration thereby preventing the clinical adaptability for individual patient needs and thereby only serves to accentuate the problem of hypotony.

The medical device in U.S. Pat. No. 5,411,473 from which this application is a continuation-in-part, includes a one-way valve (herein referred to as the Glaucoma Valve) attached to a distribution plate which collects aqueous humor drained from the patient's intraocular chamber under the control of the valve. The device is implanted in the patient's ophthalmic tissue, and within a short time after the operation, a bleb is formed around the device. A bleb is a tissue membrane that traps the aqueous humor collecting on the distribution plate. The valve opens in response to the intraocular pressure exceeding 10 millimeters (mm) of mercury (Hg) and closes once the differential pressure is below 10 mm of Hg to avoid hypotony. However, the amount of fluid capable of being collected is limited by the surface area of the distribution plate. Typically this area is about 184 square millimeters.

Glaucoma Valve

The Glaucoma Valve has many features that distinguish it from Whim and Molteno. First, it uses a membrane under tension to form a chamber having an elongated, slit-like opening therein. The membrane responds to slight changes in pressure to expand or contract to open or close the opening. When opened, it provides a wide open mouth with parted lips that allows for free flow of fluid though it without any substantial resistance to fluid flow. This feature also substantially reduces the likelihood that the opening will be clogged by particulates. Typically the width of the slit-like opening ranges between 2.500 and 3.500 millimeters, preferably between 2.725 and 2.750 millimeters.

Second, Glaucoma Valve has a chamber preferably with a trapezoidal configuration to provide a narrow side and a wide side. The slit-like opening is essentially coextensive with the narrow side and an inlet tube is connected to the wide side. Fluid flows into the chamber through the inlet tube. Depending on the fluid pressure within the chamber, the slit-like opening will be either opened or closed. The pressure in the chamber must, however, exceed the tension in the membrane in order to expand the membrane means to open the slit-like opening.

The trapezoidal configuration of the chamber renders the valve highly responsive to slight changes in pressure. The fluid, as it enters the chamber at the wide side, first flows into a space which has a relatively large cross-sectional area compared to the cross-sectional area of the chamber adjacent to the slit-like opening in the narrow side. This is important because it makes the Glaucoma Valve sensitive to slight changes in pressure and allows it to open very briefly to reduce the pressure in the chamber. When the fluid pressure in the chamber just equals the pressure created by the tension in the membrane means, the slit-like opening is closed. As soon as this pressure increases due to additional fluid flowing into the chamber along its wide side, the membrane means expands and the fluid flows from the slit-like opening. The velocity of the fluid flowing from the opening is substantially higher than the velocity of the fluid entering the chamber at its wide side to decrease quickly the pressure in the chamber and close the Glaucoma Valve. The relative high velocity with which the fluid exits the opening aids in flushing the chamber and reduces the possibility of back flow. Since the rate at which aqueous humor is formed in the intraocular chamber of the eye is very slow, approximately one drop every three hours, slight increases in volume of aqueous humor result in the valve of this invention opening momentarily and then closing. These unique features of the valve of this invention allow pressure in the chamber to be maintained at 10 mm of Hg, with an increase in pressure of 0.5 mm of Hg opening the valve. As soon as the intraocular pressure stabilizes at 10.0 mm of Hg, the valve is totally shut off to prevent the further flow of aqueous humor from draining from the intraocular chamber. Thus, the cornea never loses its dome-like shape and hypotony is avoided.

Third, the Glaucoma Valve uses two plates which hold between them in tension overlying membrane members which form between them and the chamber. The slit-like opening is along adjoining, overlapping edges of the membrane members. Preferably, the membrane members are simply two halves of a thin sheet of silastic material which is folded over upon itself. The two plates each include interlocking members that, upon the plates being pressed together, engage to place the membrane members disposed between the plates in tension. By adjusting the size and positions of the interlocking members, the tension may be varied to provide different valve designs which open in response to different pressures. Moreover, once the tension is established for a specific valve design, this Glaucoma Valve is easily reproducible, allowing this specific valve design to be mass produced without any significant variation in its pressure response from one valve to another. The interlocking members for any specific valve design apply essentially equal tension across the entire width of the membrane. This is desirable to insure repeatable performance. Each of the plates include therein identical trapezoidal shaped depressions. The plates are aligned with each other when joined together so that the two trapezoidal depressions are in registration. The trapezoidal configured chamber is formed when fluid flows between the membranes to expand them outwardly, pushing the membranes outwardly against the walls of the depressions.

SUMMARY OF THE INVENTION

The present invention is an improvement in the Glaucoma Valve by providing at least one additional distribution plate (herein the secondary distribution plate) that may be placed in any available quadrant of the eye. The secondary distribution plate is connected by a flexible connecting tube to the distribution plate (herein the primary distribution plate) attached to the Glaucoma Valve. The present invention allows the ophthalmologist to use any quadrant of the eye when implanting the primary distribution plate and any of any other quadrant of the eye for the secondary distribution plate or plates. The flexible tube allows the ophthalmologist to place the tube either above or below eye muscles when connecting the primary distribution plate to the secondary distribution plate regardless of which quadrant of the eye the secondary distribution plate is located. So, if for example, a particular quadrant had adhesions making it unacceptable for implantation, the ophthalmologist may simply by adjusting the length of the connecting tube move to another more acceptable quadrant. This feature is not present in any of the existing devices and makes this invention unique and highly desirable in the medical community.

There are several features of this invention, no single one of which is solely responsible for its desirable attributes. Without limiting the scope of this invention as expressed by the claims, its more prominent features will now be discussed briefly. After considering this discussion, and particularly after reading the section of the application entitled "DETAILED DESCRIPTION OF THE PREFERRED EMBODIMENT," one will understand how the features of this invention provide its advantages, which include (1) an increase in available surface area by up to three times or more compared to that of a single distribution plate, (2) curved distribution plates that fit the curvature of the eye, (3) adjustability to enable two or more distribution plates to be located in different quadrants of the eye, and (4) immovability of the connecting tube upon implantation of the plates.

The first feature of the medical device of this invention is that it employs a one-way flow valve. Preferably, the valve is the same or substantially similar to the Glaucoma Valve. It has a body member holding a pair of overlying elastic membranes in tension to form therebetween a chamber. The membranes provide an elongated, slit-like opening therebetween, which is normally in a closed position and opens when the pressure in the chamber exceeds a predetermined pressure and returns to the closed position when the pressure in the chamber is below said predetermined pressure. There is an inlet tube in communication with and connected to the chamber at a point remote from the slit-like opening.

The second feature is primary and secondary distribution plates in communication with each other through the connecting tube, for example, made of silicone, which is both flexible and elastic. Preferably, both the primary and secondary distribution plates are essentially oval in shape. The primary plate is connected to the one-way valve and adapted to be placed in one selected ocular quadrant of the eye. This primary distribution plate has a raised perimeter with at least one opening in the perimeter. The secondary distribution plate is adapted to be placed in another selected ocular quadrant of the eye and it also has a raised perimeter with at least one opening in the perimeter. More than one secondary distribution plate may be used, and preferably, the primary and secondary distribution plates are curved to conform to the shape of the surface of the eye. The openings in the primary and secondary distribution plates may be in the form of indentations in the top edge of the raised perimeters.

The third feature is that there are at least one pair of solid plugs, each one inserted into an opening in the perimeters of the primary and secondary distribution plates. These solid plugs are removable. Preferably, there are several openings in the perimeters of the primary and secondary plates and the solid plugs are inserted into each of these openings. One, or both solid plugs, will be removed from the perimeter of each plate upon use of the device of this invention.

The fourth feature is that there are at least one pair of secondary plugs, each having a central passageway. The secondary plugs are inserted into the openings in the perimeters of the primary and secondary distribution plates upon the removal of the solid plugs. That is one solid plug is removed from the perimeter of the primary plate and replaced with a secondary plug, and one solid plug is removed from the perimeter of the secondary plate and replaced with a secondary plug. Both the primary and secondary plugs are elastic, being made of silicone.

The fifth feature is that the connecting tube sized to fit inside the central passageway of the secondary plugs. It has opposed ends, one end being inserted in the passageway of a secondary plug in the primary distribution plate and the other end inserted in the passageway of the secondary plug in the secondary distribution plate. The distance between the primary and secondary distribution plates is adjusted by positioning the secondary plugs along the length of the connecting tube, for example, by sliding the connecting tube and secondary plugs relative to each other until the desired distance is achieved. The connecting tube thus places the primary and secondary distribution plates in fluid communication with each other. This feature assists the ophthalmologist implant the medical device of this invention in ether large or small eye balls. The flexibility of the connecting tube and the adjustability of the tube length gives the ophthalmologist the ability to place the primary and secondary distribution plates in selected quadrants and locate the connecting tube above or below eye muscles.

The sixth feature is that the diameter of the plug is slightly greater than the diameter of the opening in the perimeters of the plates and the diameter of the connecting tube is equal to, or slightly less than, the diameter of the central passageway. The secondary plugs are placed in tension to stretch them so that a secondary plug may be wedged in the opening in the perimeter of the plates upon removal of the solid plugs. When the secondary plug is placed in the opening, the tension is reduced but not completely eliminated. Thus, with the connecting tube in the passageway, and the secondary plug in the opening, but still in tension, the connecting tube remains fixed in place and is not movable after implantation of the device. The diameter of the passageways in the secondary plugs is reduced slightly to hold the connecting tube snugly but not prevent fluid flow. To further insure that the secondary plugs remain in place, the raised perimeters of the primary and secondary plates each have a predetermined thickness and the secondary plugs each have a body member with a stop element at each end thereof. The distance between the stop elements is slightly less than the thickness of the raised perimeters so that the body members are elongated when the secondary plugs are inserted into the openings. Thus, the body member is in tension with its diameter decreased slightly and its length increased, and the stop elements engaging the rim, being pulled toward each other to hold the plug snug in position in the rim.

This invention also includes a method for treating glaucoma by draining fluid from the intraocular chamber of a patient's eye. The method comprises the steps of (a) providing a medical device including a one-way flow valve attached to a primary distribution plate, said valve having an inlet tube which is placed in communication with the intraocular chamber of the eye so that the fluid drains from the intraocular chamber onto the primary distribution plate under the control of the valve, (b) providing a secondary distribution plate, said primary and secondary distribution plates each having raised perimeters with openings therein adapted to receive elastic plugs, said openings each having diameters of predetermined dimensions, (c) positioning the one-way flow valve with the attached primary distribution plate in a selected ocular quadrant of the eye and providing a connecting tube having opposed ends at which are elastic plugs which each have a passageway therein that receives the connecting tube, (d) positioning the secondary distribution plates in another selected ocular quadrant of the eye and placing the primary distribution plate and the secondary distribution plate in communication with each other through the connecting tube by inserting one plug into the opening in the perimeter of the primary distribution plate and inserting the other plug into the opening in the perimeter of the secondary distribution plate, with the distance between the plates being adjusted to approximately equal the distance between the primary and secondary plates, each plug having a diameter slightly greater than the diameter of the opening in which it is inserted, (e) stretching the plugs prior to inserting them into the openings and then releasing the plugs after insertion so that the plugs fit snugly in the openings and the diameter of the passageways in the plugs is reduced slightly to hold the connecting tube snugly but not to prevent fluid flow.

DESCRIPTION OF THE DRAWING

The preferred embodiments of this invention illustrating all of its features will now be discussed in detail. These embodiments depict the novel and unobvious features of the medical device of this invention. The drawing accompanying this application, which is for illustrative purposes only, includes the following figures (FIG.), with like numerals indicating like parts:

FIG. 25 is a plan view showing the primary distribution plate with an attached one-way valve.

FIG. 26 is a cross-sectional view along line 26—26 of FIG. 25.

FIG. 27 is a cross-sectional view along line 27—27 of FIG. 25.

FIG. 28 is an enlarged fragmentary view taken along line 28 of FIG. 25.

FIG. 29 is an enlarged fragmentary view taken along line 29 of FIG. 25.

FIG. 30 is an enlarged fragmentary view taken along line 30 of FIG. 26.

FIG. 31 is an enlarged fragmentary view taken along line 31 of FIG. 27.

FIG. 32 schematically depicts an ophthalmologist pulling gently on the ends of a secondary plug in order to position the center of the plug in the opening of the perimeter wall of a distribution plate.

FIG. 33 is a cross-sectional view along line 33—33 of FIG. 31.

DETAILED DESCRIPTION OF THE PREFERRED EMBODIMENTS

Figure 1:
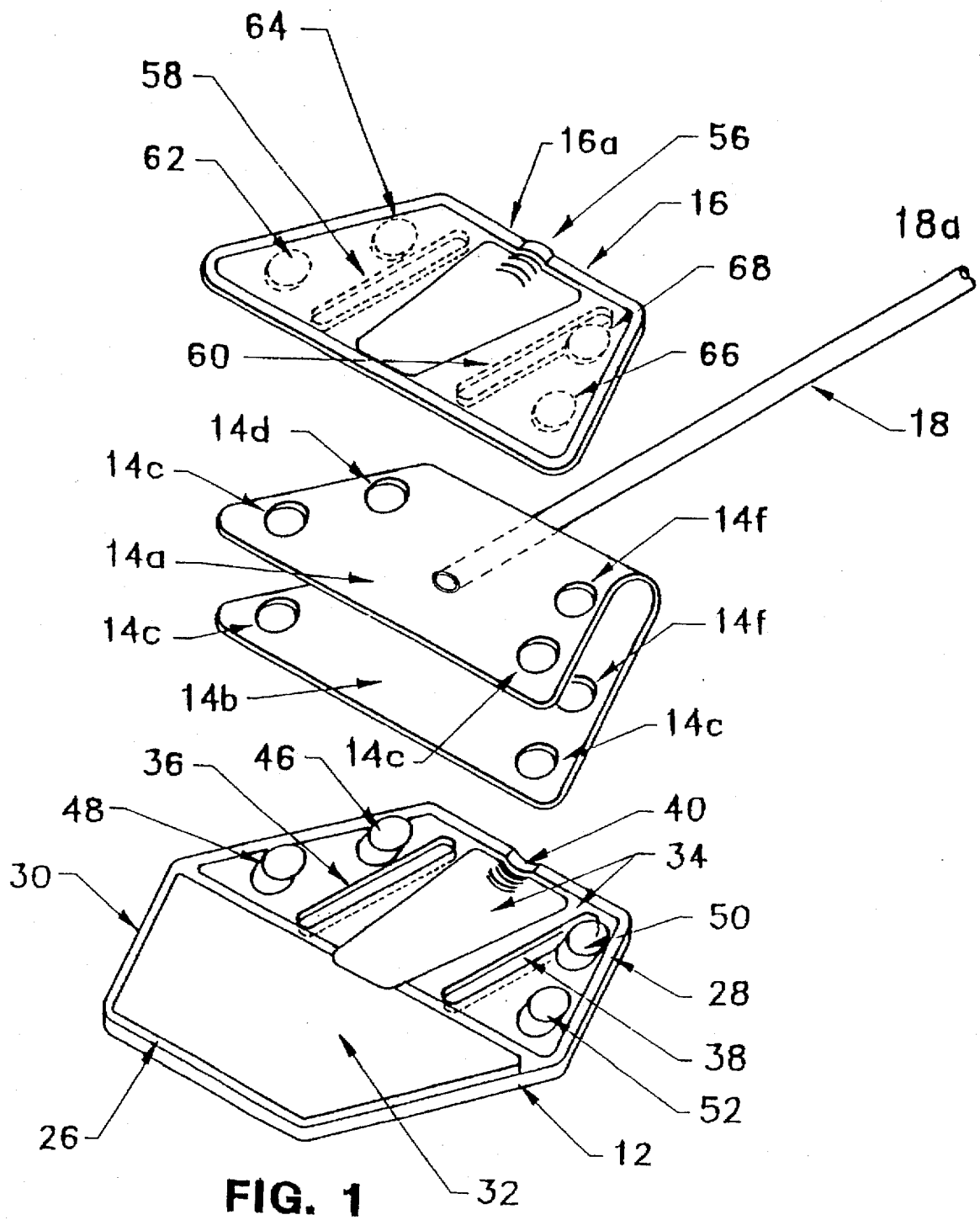
FIG. 1 is an exploded perspective view of the medical valve of this invention.
Figure 3A:
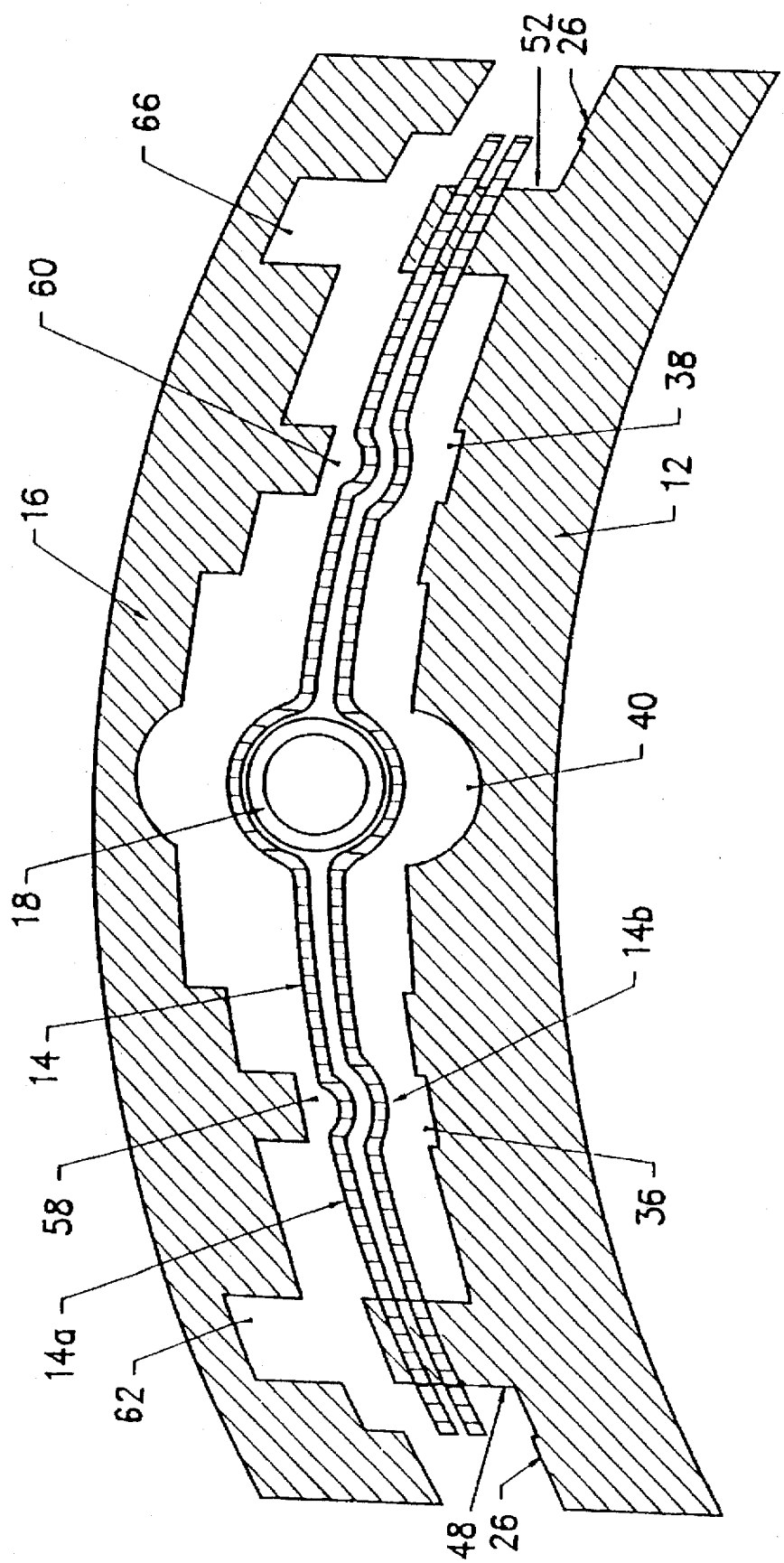
FIG. 3A is a cross-sectional view showing the two plates positioned to be pressed together to hold the folded membrane therebetween.
Figure 3B:
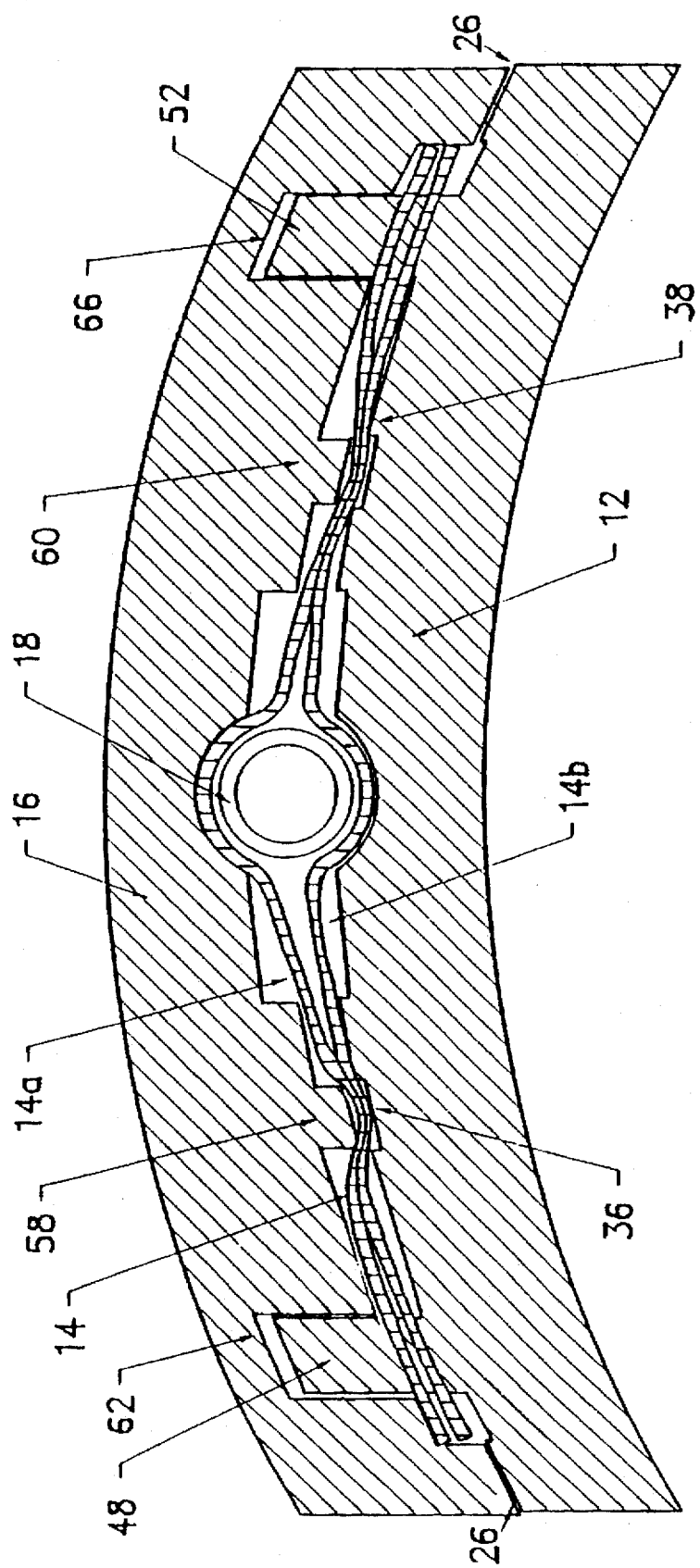
FIG. 3B is a cross-sectional view showing the two plates connected together and holding the folded membrane therebetween.
Figure 4:
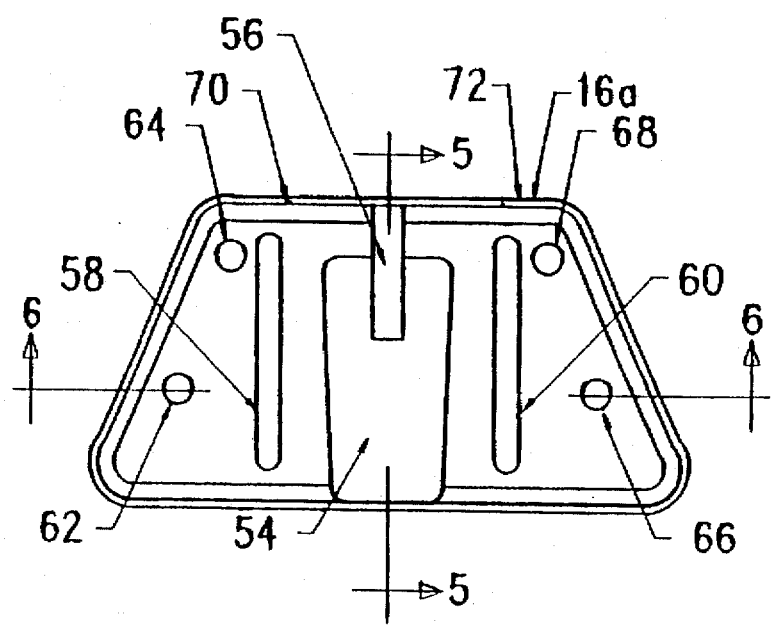
FIG. 4 is a plan view looking at the internal surface of the top plate used in the medical valve of this invention.
Figure 5:
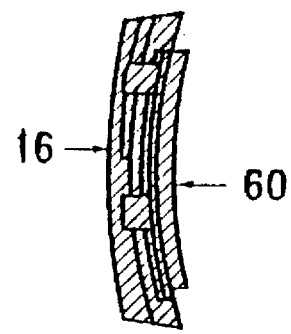
FIG. 5 is a cross-sectional view taken along 5—5 of FIG. 4.
Figure 6:
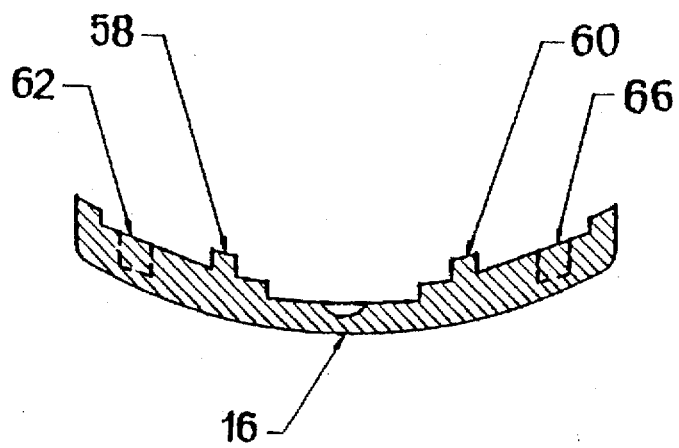
FIG. 6 is a cross-sectional view along 6—6 of FIG. 4.
Figure 7:
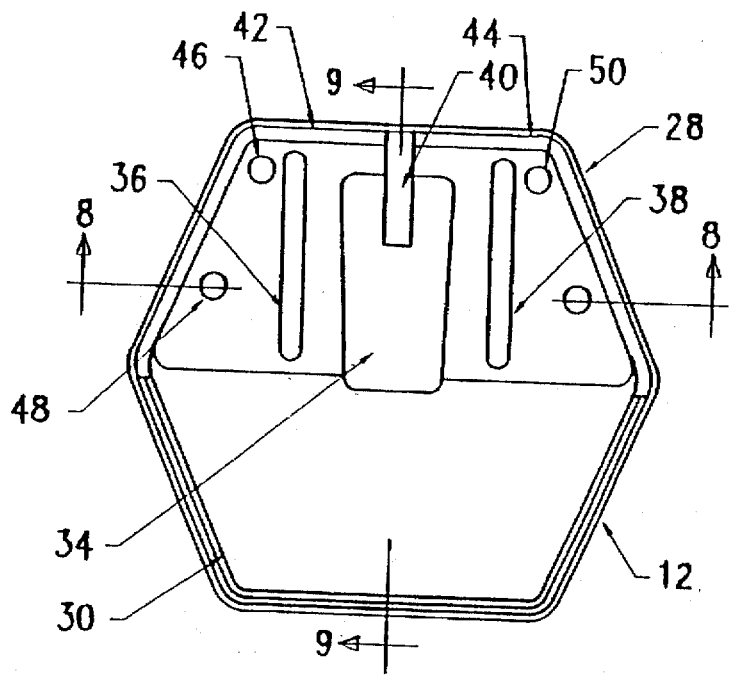
FIG. 7 is a plan view showing the internal surface of the base plate used in the medical valve of this invention.
Figure 9:
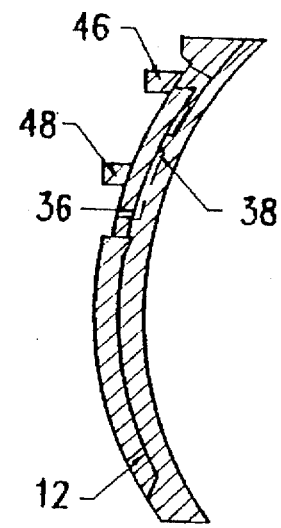
FIG. 9 is a cross-sectional view taken along 9—9 of FIG. 7.
Figure 8:
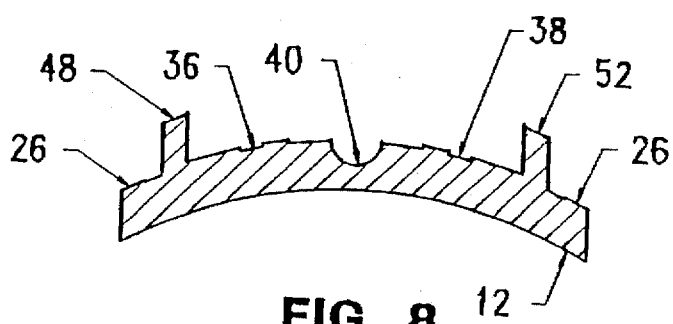
FIG. 8 is a cross-sectional view taken along line 8—8 of FIG. 7.
Figure 15:
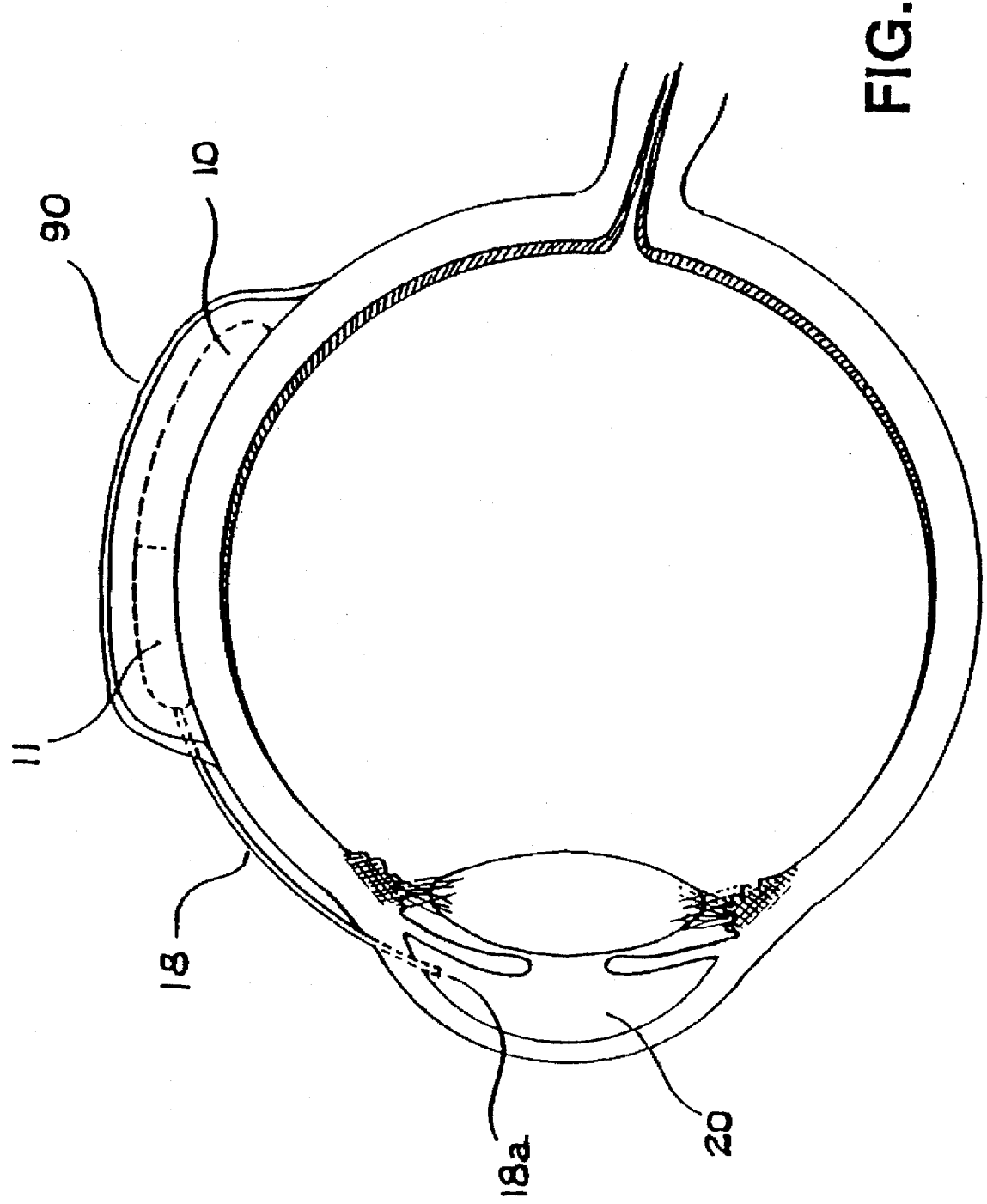
FIG. 15 is a cross-sectional view of the eyeball of the patient with the medical valve of this invention implanted therein.

As best illustrated in FIG. 1, the medical valve 10 of this invention includes a base plate 12, a flexible, silicone membrane 14, a top plate 16, and a silicone inlet tube 18. The membrane 14 is folded to form a pair of essentially identically shaped membrane members 14a and 14b. The membrane members 14a and 14b are placed between aligned and spaced apart top plate 16 and base plate 12 as illustrated in FIG. 3A and these plates are pressed together and interlocked as illustrated in FIG. 3B to hold the membrane members in position. The inlet tube 18 extends from the plates 12 and 16 so that its free end 18a may be surgically inserted into the intraocular chamber 20 of the eye as illustrated in FIG. 15.

Figure 2:
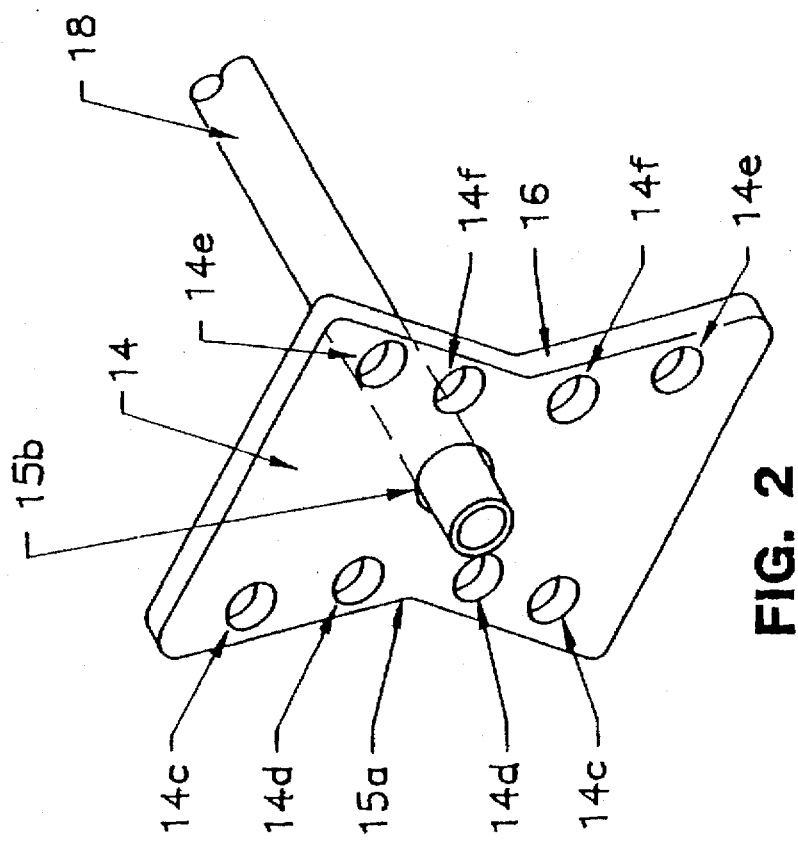
FIG. 2 is a perspective view of an unfolded membrane, with a tube extending outwardly from its backside.
Figure 2A:
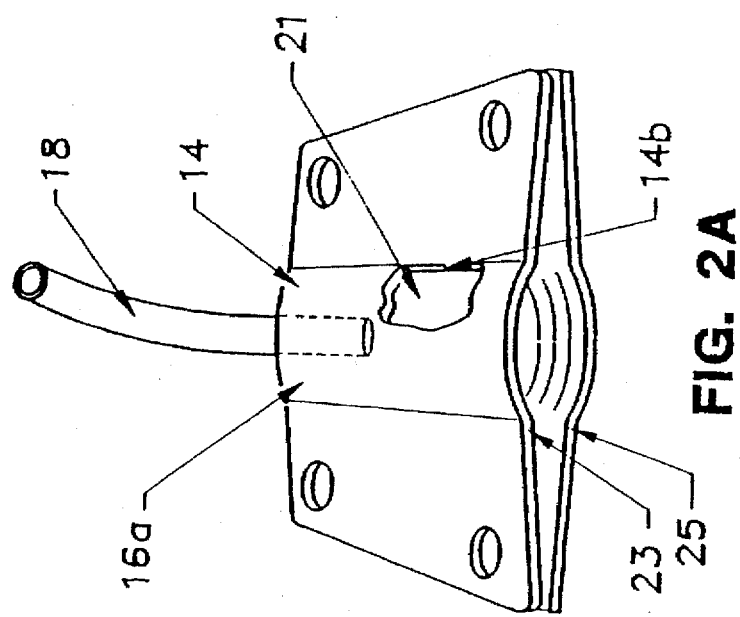
FIG. 2A is a perspective view of the membrane folded to form a trapezoidal chamber, showing the slit-like opening with its lips parted to allow fluid to flow from the chamber.

The membrane 14 is originally in a non-folded condition as shown in FIG. 2, and it has an hourglass-like shape narrowing at the central section 15a and then expanding outwardly therefrom in both directions. The membrane 14 has a thickness ranging between 0.004 and 0.007 inch, preferably between 0.005 and 0.006 inch. There is a central opening 15b in the member 14 in which the inlet tube 18 is inserted and four spaced apart openings 14c, 14c', 14d, 14d', 14e, 14e', 14f, and 14f' along its opposed irregular sides 22 and 24. These holes 14c through 14f and 14c' through 14f' have a diameter of approximately 0.02 inch. A suitable silicone material for use as the membrane 14 and inlet tube 18 is made by Dow Corning Corporation, Medical Products, identified by the tradename Silastic, product No. 602-105.

The base plate 12 has a generally hexagonal configuration with a raised ridge 26 extending above the perimeter of the plate. The plate 12 is divided into a forward section 28 and a rear section 30. The portion of the ridge 26 surrounding the rear section 30 forms a distribution area 32 which receives aqueous humor from the eye. This distribution area 32 preferably ranges between about 0.119 and about 0.200 square inch.

The forward section 28 is raised above the distribution area 32 and it includes a centrally located depression 34 of a generally trapezoidal configuration. On each side of this depression, running along substantially its entire length, are two grooves 36 and 38. At the one end 34a of the depression 34 is a semi-cylindrical indentation 40 which receives the tube 18 and on each side of this indentation are two tiny orifices 42 and 44 having a diameter of about 0.02 inch. On the outside of each of the two grooves 36 and 38 are a pair of raised pins 46 and 48 and 50 and 52, respectively.

The top plate 16 is a four-sided member having a centrally located trapezoidal depression 54 therein with a semi-cylindrical indentation 56 along its one side 16a. There are a pair of elongated finger elements 58 and 60 extending downwardly which interlock, respectively, in the grooves 36 and 38 in the base plate 12 when the two plates are pressed together. There are pairs of bores 62 and 64 and 66 and 68, respectively, of on the outside of each of the fingers 58 and 60 which receive the pairs of pins 46 and 48 and 50 and 52 in the base plate 12 when the top plate 16 and base plate are aligned and pressed together. There are two small orifices 70 and 72 in the top plate 16 which are in registration with the orifices 42 and 44 when the base plate and top plate are joined together.

Both the top and base plates 12 and 16 have a segmented spherical shape so that they conform to the curvature of the eye ball. Both the plates 12 and 16 and the tube 18 are made of a material that will not be rejected by the body. Suitable materials from which to make the plates 12 and 16 are silicone, polypropylene, and polymythlmethyl acrylate (PMMA).

Figure 10:
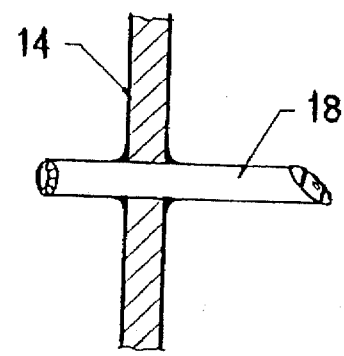
FIG. 10 is an enlarged cross-sectional view showing the way the tube is connected to the membrane.
Figure 11:
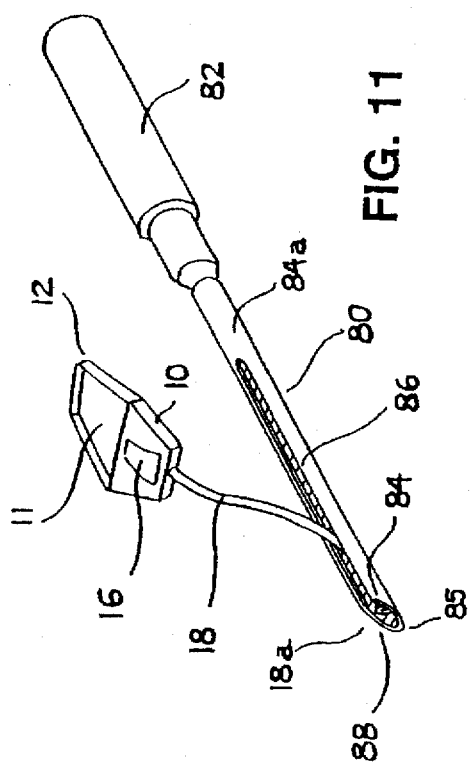
FIG. 11 is a perspective view of a novel surgical instrument of this invention used to insert the tube from the valve into the intraocular chamber of the eye.
Figure 12:
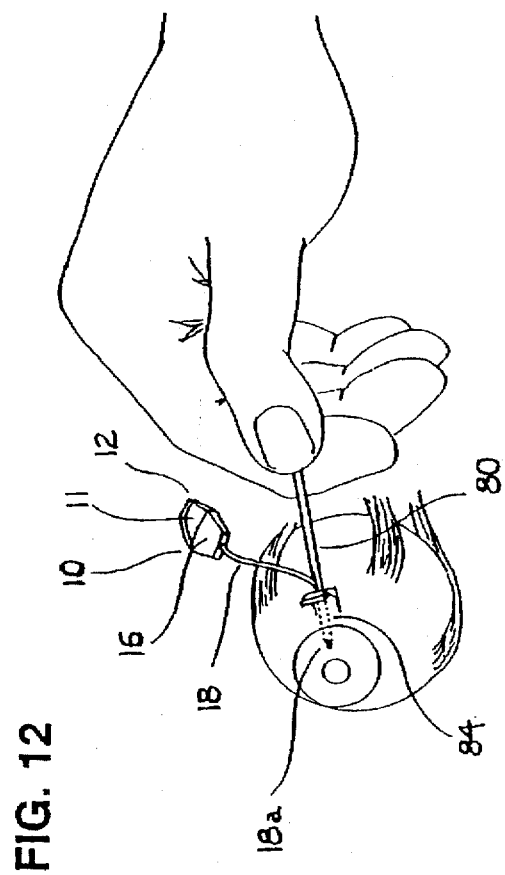
FIG. 12 is a schematic view showing the valve of this invention being surgically implanted in the eye of a patient using the instrument shown in FIG. 11.

FIG. 10 shows the way that the inlet tube 18 is bonded to the membrane 14. With the membrane 14 folded inwardly upon itself, it is placed between the top plate 16 and base plate 12 and these plates are interconnected together. This inlet tube 18 is inserted into the central opening 15b, with its outwardly extending section being placed between the indentations 40 and 56, respectively, in the plates 12 and 16. As shown in FIG. 10, an adhesive 17 is used to bond the tube 18 and the membrane 14. An example of a suitable adhesive is medical grade Silastic A made by Dow Corning Corporation.

One of the unique features of this invention is that, when the plates 12 and 16 are joined together, the membrane members 14a and 14b form between them in the space between the trapezoidal indentations 34 and 54 a chamber 21. At the inward edges 74 (FIG. 1) of these members 14a and 14b there is formed adjoining lips 23 and 25 that provide an elongated, slit-like opening 19 in the chamber 21 that is unlikely to be clogged by particulates. This slit-like opening 19 is normally closed because of the tension in the membrane members 14a and 14b, but opens when the pressure across the opening exceeds a predetermined value. When used as a glaucoma valve, the differential in pressure must exceed 10 millimeters of mercury before the lips 23 and 25 part to open the valve. These lips 23 and 25 close immediately when the pressure differential is less than 10 millimeters of mercury.

The chamber 21 formed between the members 14a and 14b has a trapezoidal configuration. This is important because it makes the valve 10 very sensitive to slight changes in pressure. Due to the trapezoidal configuration of the chamber 21, the area of the inlet end of the chamber is larger than the area of the outlet end of the chamber. This creates a Bernoulli effect. Specifically, the incoming fluid fills the chamber 21 and the pressure increases to the point where the lips 23 and 25 of the membrane members 14a and 14b forming the slit-like opening 19 spread apart. The fluid then flows through the parted lips 23 and 25 of the membrane members 14a and 14b at a velocity which is substantially higher than the velocity of the fluid entering the chamber at the inlet end. Thus, the pressure is reduced almost instantaneously to close the valve 10. The incoming fluid causes the pressure in the chamber 21 to once again increase and the valve 10 again opens, with the pressure in the chamber deviating only slightly from a nominal value corresponding, for example, to the desired pressure to be maintained in the intraocular chamber of the eye, namely 10 mm of Hg.

The medical valve 10 of this invention is easy to assemble. The membrane 14 is simply folded over and placed between the base plate 12 and top plate 16 with these plates aligned and in registration so that, when they are pushed together, the interlocking members, including the pins 46, 48, 50 and 52 and bores 62, 64, 66, and 68, and grooves 36 and 38, and fingers 58 and 60, clamp the membrane members 14a and 14b firmly between the plates to form the valve body 11. The pins 46, 48, 50, and 52 pass through the holes 14c through 14f upon joining the plates 12 and 16 together. Ultrasonic welding bonds the plates 12 and 16 together.

As best illustrated in FIGS. 11 through 15, the medical valve 10 of this invention may be inserted into the eye of a patient by the use of a unique surgical instrument 80 consisting of a handle 82 and needle-like body member 84 having an elongated slot 86 in a side wall 84a of the needle-like member. The needle-like body member 84 terminates at the shape tip 85 which is beveled. The slot 86 allows the inlet tube 18 to be placed within the needle-like body member 84 lengthwise along a U-shaped channel 88 running along the longitudinal axis of the needle-like body member. The slot 86 and channel 88 each have a width that is essentially equal to the diameter of the inlet tube 18 so that, with the inlet tube lying in the channel, there is a snug, friction fit. Thus, fluid enters the open end of the tube and flows through the tube 18 rather than between the wall of the channel 88 and the wall of the tube. For use with the glaucoma valve 10 of this invention, the slot 86 has a width from 0.025 to 0.028 inch and a length of from 1.1 to 1.25 inch. The dimensions of the slot and channel may, however, be varied depending on the application.

Figure 14:
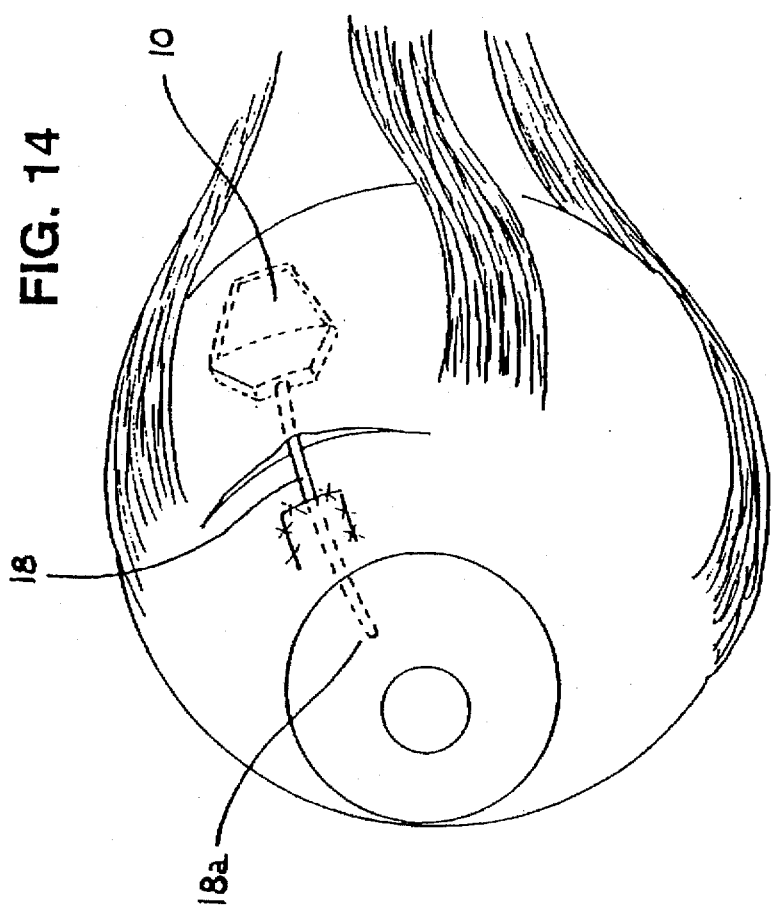
FIG. 14 is a perspective view of the valve implanted in the eye of a patient.
Figure 13:
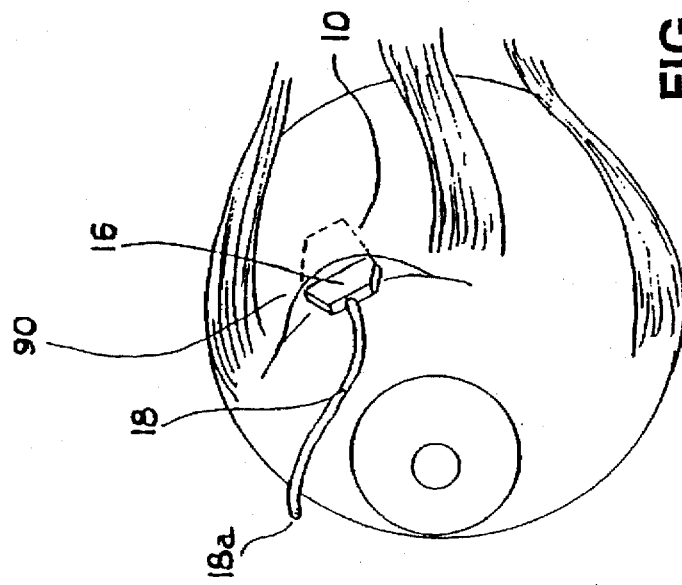
FIG. 13 is an enlarged perspective view of the medical valve of this invention partially implanted into the eye of the patient.

To use the instrument of this invention, with the tube 18 in the channel 88, the ophthalmologist simply inserts the shape tip 85 of the instrument 80 into the eyeball to bring the inlet tube 18 into the intraocular chamber 20 of the eye. The ophthalmologist then simply withdraws the instrument. As he does this, the inlet tube 18 remains in the eye, with the surrounding tissue grasping the inlet tube as the instrument 80 is withdrawn. The valve body 11 is then placed beneath a sclera flap 90 (FIGS. 13 and 14) which is cut from the exterior of the eye ball. The flap 90 is then placed over the valve body 11 and then sutured in position as shown in FIG. 14. The aligned orifices 42 and 44 and 70 and 72, respectively in plates 12 and 16, allow the ophthalmologist to suture the valve body 11 to the eye ball. This allows any overflow of aqueous humor flowing from distribution area 32 to seep beneath the valve body 11.

Figure 16:
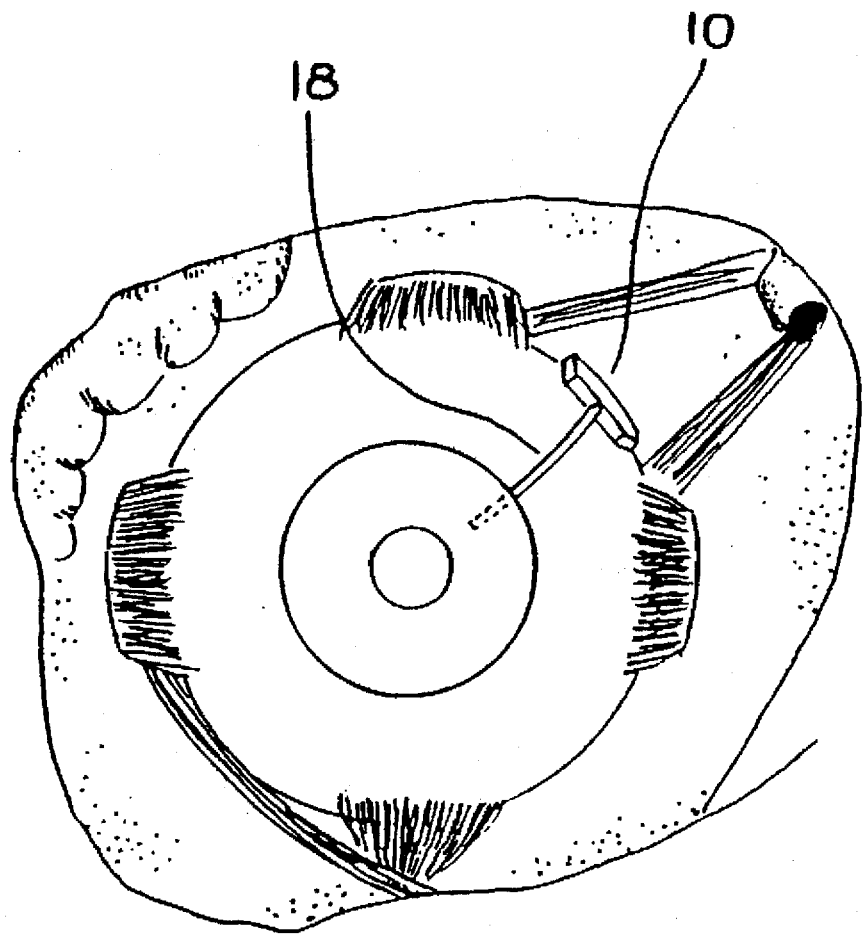
FIG. 16 is a front elevational view of an eye ball with the medical valve of this invention positioned at the desired location on the exterior of the eyeball.

Within a short period of time after the operation, a bleb is formed around the valve body 11. A bleb is a tissue membrane that traps the aqueous humor collecting in the distribution area 32 or under the valve body 11. This entrapped fluid is then slowly absorbed into the body of the patient. With the valve 10 implanted in the patient, as illustrated in FIGS. 1S and 16, pressure within the intraocular chamber 20 forces the aqueous humor through the inlet tube 18 into the trapezoidal chamber. When the chamber is filled and the pressure in the intraocular chamber 20 exceeds 10 millimeters of mercury, the lips 23 and 25 formed by the overlying members 14a and 14b spread apart, but only for such time period as this differential pressure exists. Once the differential pressure is below 10 millimeters of mercury, the membrane members 14a and 14b, being under tension, close off the slit-like opening 19 automatically so that aqueous humor no longer will escape from the intraocular chamber 20, thereby avoiding hypotony.

First Alternate Embodiment

Figure 22:
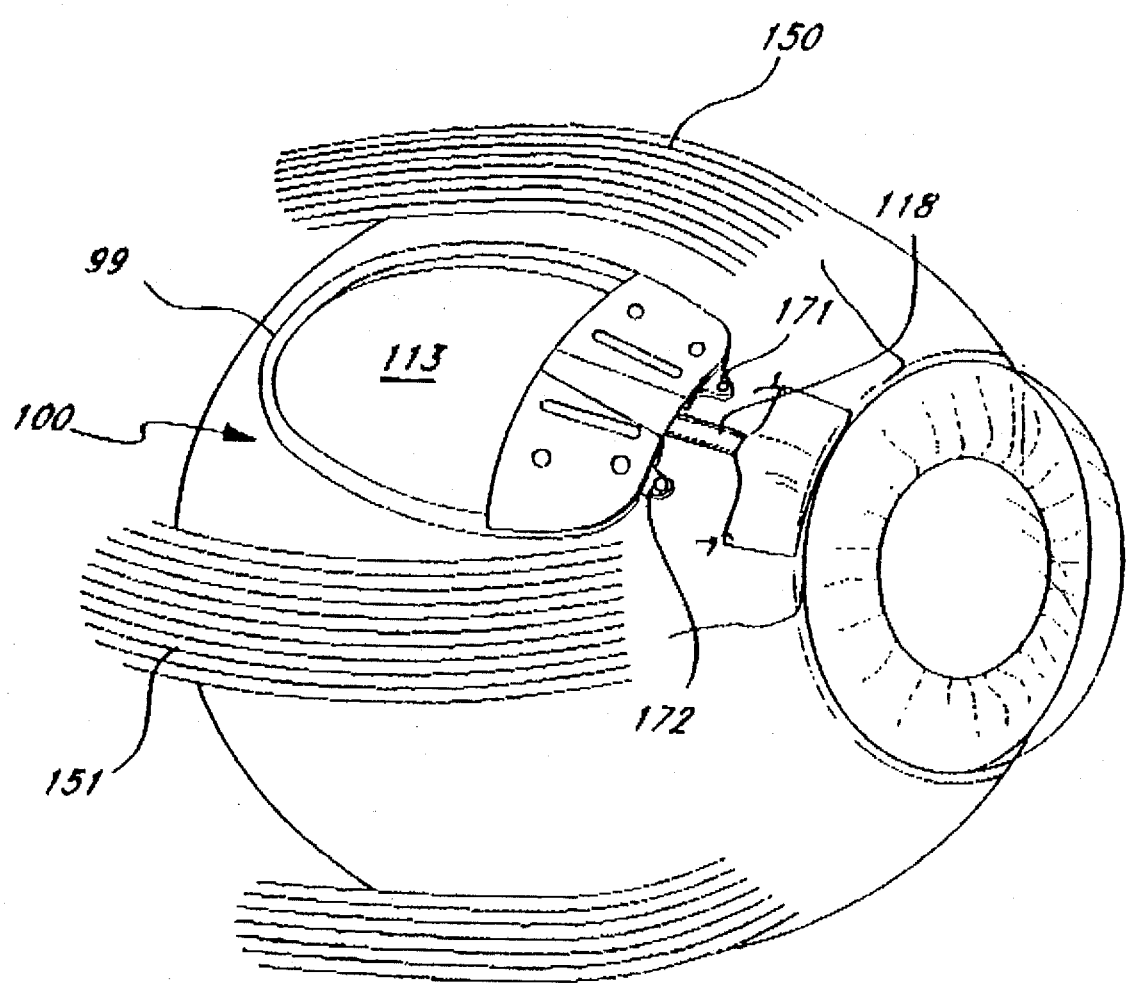
FIG. 22 is a perspective view showing the valve of FIG. 17 attached to the exterior of an eye and located so that its tapered end is positioned between eye muscles.

The alternate embodiment of this invention, the valve 100, is similar in many respects to the valve 10 depicted in FIG. 1, with the principal difference being that this new valve 100 has a uniquely shaped body member 101. The valve 100 has a base plate 112, a top plate 116 with a folded membrane 114 sandwiched between these plates. An inlet tube 118 extends outward from the folded portion of the membrane 114, with the overlapping membrane members 114a and 114b being held in position by pins 146, 148, 150, and 152 which extend through openings 115 in the membrane and into bores 162, 164, 166, and 168 in the top plate 116. Finger elements 158 and 160 extending from the bottom of the top plates are wedged into grooves 136 and 138 in the forward section 128 of the base plate. This causes the membrane 114 to stretch, placing it in tension so that a slit-like opening is formed between the edges of the overlapping membrane members 114a and 114b. There are trapezoidal depressions 134 and 154, respectively, in the base plate 112 and the top plate 116. This creates a trapezoidal-shaped chamber (not shown) between the overlapping membrane members 114a and 114b into which fluid exiting the inlet tube 118 flows. There are a pair of extensions 169 and 171 along the anterior edge 97 of the base plate 112 with orifices 170 and 172 therein that allow the valve 100 to be sutured to the an eyeball as depicted in FIG. 22.

Figure 18:
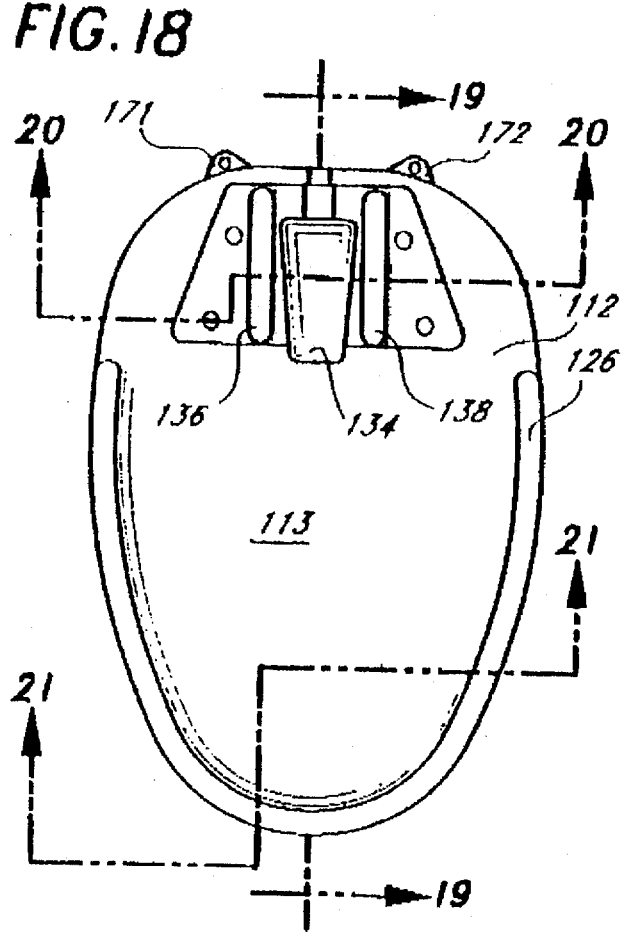
FIG. 18 is a plan view of the base plate used in the valve shown in FIG. 17.
Figure 19:
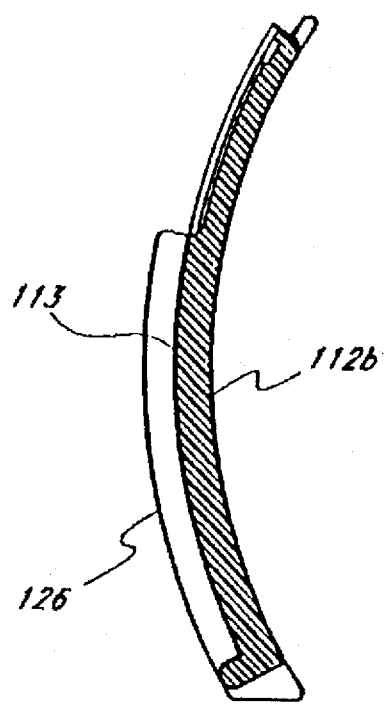
FIG. 19 is a cross-sectional view taken along line 19—19 of FIG. 18.
Figure 20:
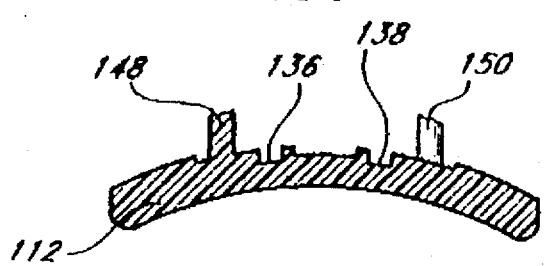
FIG. 20 is a cross-sectional view taken along line 20—20 of FIG. 18.
Figure 21:
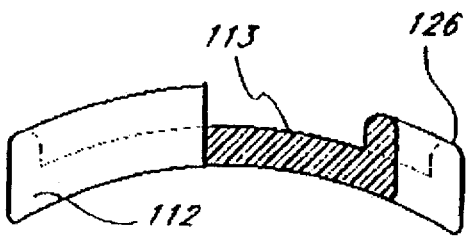
FIG. 21 is a cross-sectional view taken along line 21—21 of FIG. 18.

In accordance with one of the principal features of this embodiment of this invention, the body member 101 has a generally oval shape as best illustrated in FIG. 18. The base plate 112 is in the form of a segmented sphere, providing a concave interior surface 112b which rest against the eyeball when the valve 100 is implanted in, for example, a glaucoma patient. As with the Glaucoma Valve, the inlet tube 118 has its remote end inserted into the ocular chamber of the eye allowing the aqueous humor to drain from the eye when pressure in the ocular chamber is excessive. The valve 100 opens under the influence of this excessive pressure to allow the aqueous humor to drain onto the enlarged surface area 113 surrounded by the raised ridge 126 on the base plate 112.

Figure 17:
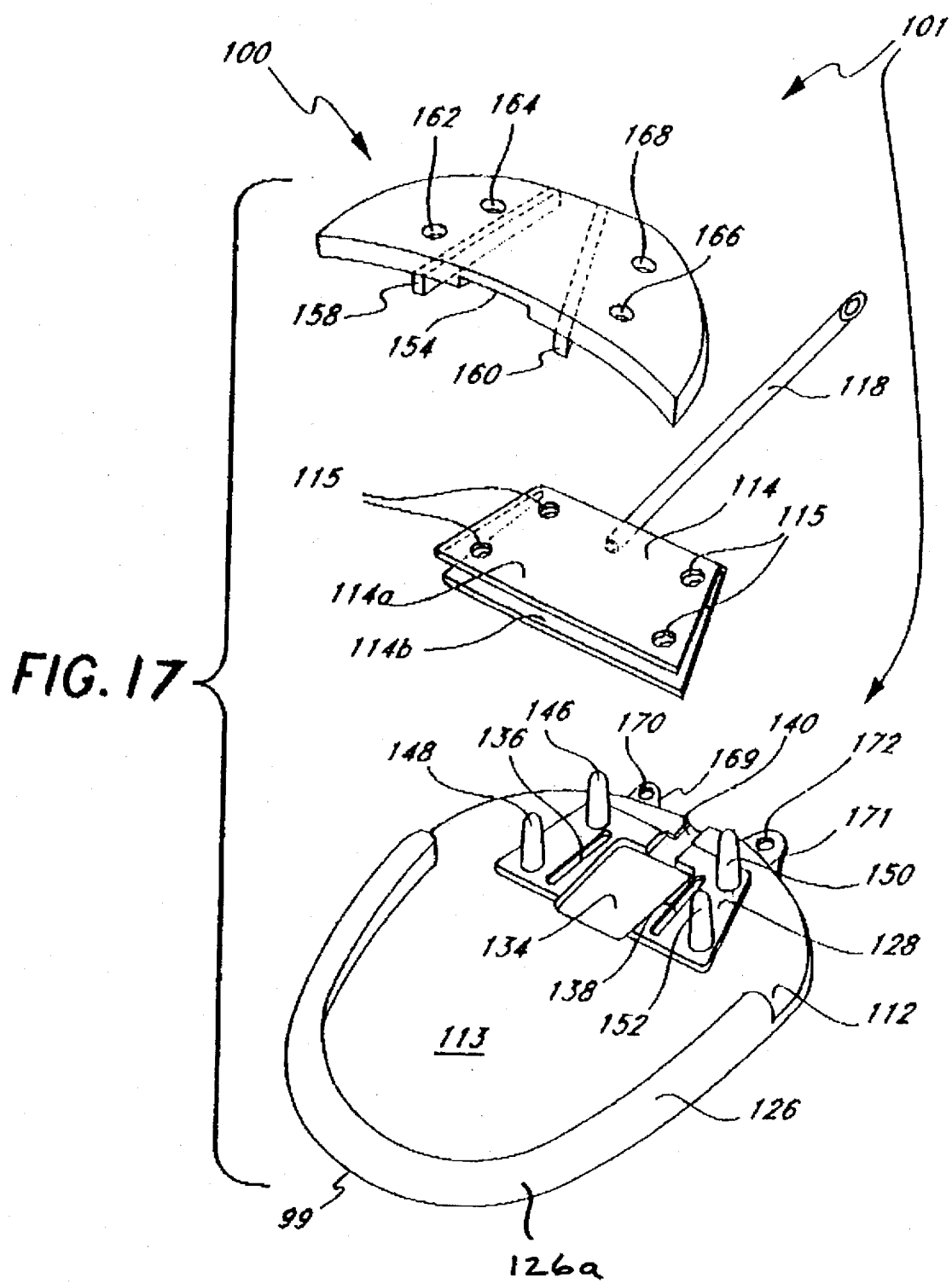
FIG. 17 is an exploded perspective view of an alternate embodiment of this invention having a unique shape.

As best depicted in FIG. 17, the posterior edge 99 of the valve 100 is tapered so that it fits easily between the major rectus muscle 150 and minor rectus muscle 151 of the eyeball. This allows the valve 100 to be inserted as shown with the tapered end pointing towards the posterior of the eyeball. Typically, the valve 100 has a width ranging between 7 and 13 millimeters, and a length ranging between 10 and 16 millimeters. This allows for the provision of a substantially increased surface area 113, maximizing utilization of the area between the major and minor rectus muscles in the most efficient manner, for example the surface area 113 is about 0.3 square inch. The anterior edge 97 of the valve is approximately 8 to 12 millimeters from the limbus when the valve is positioned as illustrated in FIG. 22.

There is a ridge 126 surrounding the enlarged surface area 113 which assist in formation the bleb 90. The ridge 126 has an exterior wall 126a which tapers inward towards the enlarged surface area 113. Thus, the wall of the bleb will form a complementary angle also lying inward towards the enlarged surface area 113. The ridge 126 also retains fluid on the enlarged surface area 113.

As with the valve illustrated in FIG. 1 and FIG. 15, a sclera flap 90a is cut from the exterior of the eyeball and the valve 100 is placed underneath this flap. This forms a bleb which surrounds the valve 100. Because of the difference in length versus the width of the valve 101, i.e., its the oval configuration, the bleb is more porous than if the valve was circular. Consequently, the aqueous humor collected on the enlarged surface area 113 more readily absorbs into the patient's body.

In accordance with the method of this invention, the valve 100 is placed between the major and minor rectus muscles as opposed to inserting the valve underneath these muscles as is the case with some ocular implant devices. The placement of the valve as depicted in FIG. 22 is highly desirable, since it minimizes the problems associated with strabism, or eye squinting, which is frequently caused when ocular devices are positioned underneath the major and minor rectus muscles.

Second Alternate Embodiment

Figure 23:
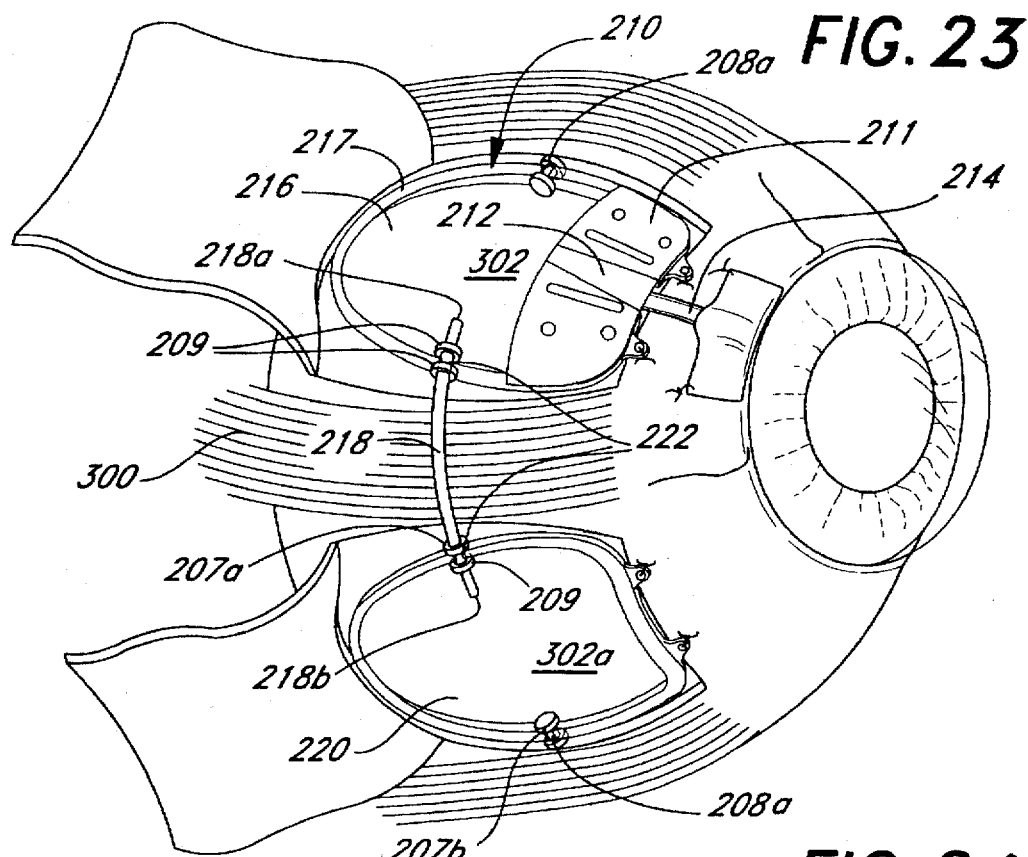
FIG. 23 is a perspective view of the medical device of this invention being implanted, showing the secondary distribution plate connected to the primary distribution plate which is in an upper quadrant of the eye.
Figure 24:
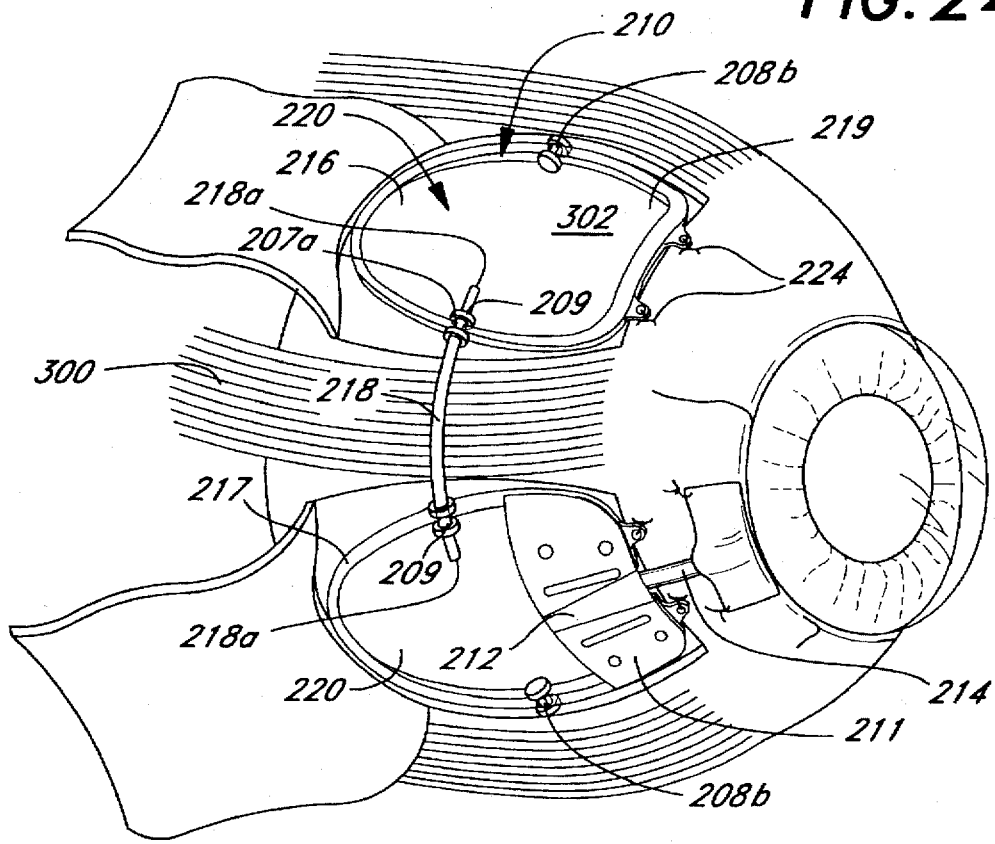
FIG. 24 is a perspective view of the medical device of this invention being implanted, showing the secondary distribution plate connected to the primary distribution plate which is in a lower quadrant of the eye.

As best illustrated in FIGS. 23 and 24, another embodiment of this invention, the medical device 210, includes a valve and distribution plate assembly 212 and a secondary distribution plate 220. The valve and distribution plate assembly 212 and the secondary distribution plate 220 are in communication with each other through a flexible connecting tube 218. In accordance with this invention, the connecting tube 218 is selectively connected between different connection points on the valve and distribution plate assembly 212 and the secondary distribution plate 220. This enables the ophthalmologist to select one quadrant of the eye in which to place the valve and distribution plate assembly 212 and another quadrant of the eye in which to place the secondary distribution plate 220. As illustrated, the flexible connecting tube 218 is over the eye muscle 300, but it could be place beneath this muscle.

FIG. 23 shows the valve and distribution plate assembly 212 in an upper quadrant, and FIG. 24 shows the secondary distribution plate 220 in the upper quadrant. Two opposed connection points in both the valve and distribution plate assembly 212 and the secondary distribution plate 220 permit this type of selectivity in location. There are suturing holes 224 in both the valve and distribution plate assembly 212 and the secondary distribution plate 220, enabling these structures to be attached to the eye. Both the valve and distribution plate assembly 212 and the secondary distribution plate 220 are located under an ophthalmic membrane, which is depicted as being drawn back for illustration purposes only. This membrane is actually slit in two different places, with valve and distribution plate assembly 212 inserted into one of the slits and the secondary distribution plate 220 inserted into the other slit. Upon healing a separate bleb is formed around both the valve and distribution plate assembly 212 and the secondary distribution plate 220.

The valve and distribution plate assembly 212 includes a one-way valve 211 (preferably the Glaucoma Valve), an essentially oval shaped primary distribution plate 216 affixed to the valve 211, and an inlet tube 214 connected to the the valve 211. As best illustrated in FIGS. 23 and 24, the free end of the inlet tube 214 is inserted into the intraocular chamber of the eye of a patient. Aqueous fluid enters the inlet tube 214 when the intraocular pressure exceeds 10 mm of Hg. The fluid flows through the tube 214 into and through the valve 211 and out onto the primary distribution plate 216.

The primary distribution plate 216 has a raised rim 217 encompassing a collection zone 302 with two directly opposed openings 207a and 207b in the rim 217. These openings 207a and 207b serve as the connection points for an end of the connecting tube 218. The openings 207a and 207b are in the form of indentations in the top edge 217a of the rim 217. The secondary distribution plate 220 includes a central collection zone 302a surrounded by a rim 219. Prior to implantation of the device 210, this rim 219 also has two opposed indentations 207a and 207b which initially have insert therein solid plugs 208a and 208b. As shown in FIGS. 23 and 25, one of these solid plugs 208b is removed from the rim 217 of the primary distribution plate 216 and replaced with a secondary silicone plug 209. The other solid plug 208a remains in place in the rim 217. As best shown in FIGS. 28, 30, and 31, each secondary plug 209 is an integral piece injected molded from silicone. It has a central, cylindrical body 250 with enlarged, disk-like circular end caps 251, with an elongated passageway 222 (FIG. 33) extending through the body between the end caps. The solid plugs 208a and 208b are similarly constructed, except there are no passageways in these solid plugs.

Selectively, depending on which quadrants of the eye the secondary distribution plate 220 and primary distribution plate 216 are located, the solid plugs 208a and 208b are removed and replaced with secondary plugs 209. In FIG. 23, both solid plugs 208b in the primary distribution plate 216 and the secondary distribution plate 220 have been removed from the opening or indentations 207a and 207b and replaced with a secondary plug 209. In FIG. 24, both solid plugs 208a in the primary distribution plate 216 and the secondary distribution plate 220 have been removed from the indentations 207a and 207b and replaced with a secondary plug 209. The connecting tube 218 is sized to pass through the passageway 222 of the secondary plugs 209, but fits snugly yet allows the secondary plugs to slide along its length to adjust the distance between the plugs at the ends of the connecting tube. Thus, the primary distribution plate 216 is in fluid communication with the secondary distribution plate 220 via the connecting tube 218 passing through secondary plugs 209 in these plates. The secondary distribution plate 220 receives the overflow of aqueous humor from the primary distribution plate 216.

As illustrated in FIG. 23, the passageway 222 receives one end 218a of the connecting tube 218, which passes through the passageway. The second end 218b of the connecting tube 218 passes through another passageway 222 in another secondary plug 209 inserted an opening in the raised rim 219 of the secondary distribution plate 220 upon removal of the solid plug. One of the advantages of this invention is that both the primary distribution plate 216 and the secondary distribution plate 220 each have a right and left hand solid plugs 208a and 208b. This plug location in the perimeters of the plates enables the ophthalmologist to selectively remove a plug for either right or left hand access. Either one or both of these solid plugs 208a and 208b may be replaced with a secondary plug 209. The conventional Molteno plate, for example, is either a right or a left hand plate. This sometimes causes confusion. The present invention is not so limited, since the secondary distribution plate 220 may be attached to either the right of left side of the primary distribution plate 216.

In use, the connecting tube 218 comes already assembled with the secondary plugs 209 at opposed ends of this tube. The distance between the secondary plugs 209 must be about equal to the distance between the primary distribution plate 216 and the secondary distribution plate 220, which have been previously implanted in the patient's eye in the selected quadrants of the eye. The ophthalmologist adjusts the position of the secondary plugs 209 relative to the connecting tube 218 to equal the distance required to reach between the two selected quadrants by sliding the plugs along the length of the connecting tube 218. After making this adjustment, the ophthalmologist may, if desired, cut the excess tube extending beyond the distal ends 209c of the secondary plugs. The ophthalmologist removes the solid plugs, plug 208a or 208b as the case may be, in both the primary distribution plate and the secondary distribution plate and replaces them with the secondary plugs 209 already attached to the ends of the connecting tube 218. In accordance with this invention, the central body 250 of each of the secondary plugs is slightly greater in diameter than the diameter of the openings 207a and 207b in the perimeters of the plates and the diameter of the connecting tube 218 is equal to, or slightly less than, the diameter of the passageway. This enables the plugs 209 to nest snugly within the openings 207a and 207b to prohibit fluid leakage from the opening site. The solid plugs 208 also nest tightly in these opening 207a and 207b in which they are seated to prohibit fluid leakage from the opening site.

As best shown in FIG. 32, the ophthalmologist places each secondary plug 209 in tension by grasping the end caps 251 to stretch the central body 250 so that a secondary plug 209 may be wedged in an opening, for example opening 207a in the perimeter of the plate 216, upon removal of a solid plug. The distance between the end caps 251 is slightly less than the thickness t of the rim 217 so that the body 250 is elongated when the secondary plug 209 is inserted into the opening 207a. Thus, the body 250 is in tension, with its diameter decreased slightly and its length increased, and the end caps 251 engaging the sides of the rim 217, being pulled toward each other to hold the plug 209 snug in position in the rim. When the secondary plug 209 is so placed in an opening, the tension is reduced upon release of the grip of the ophthalmologist, but not completely eliminated. Thus, with the connecting tube 218 in the passageway 222, and the secondary plug 209 in tension in an opening, the connecting tube remains fixed in place and is not movable after implantation. The secondary plug 209 fits snugly in the opening 207a and prevents leakage of the fluid or movement of the tube 218. If a third or fourth distribution plate is needed, the above process is repeated and additional secondary distribution plates 220 are implanted in other quadrants of the eye.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

I claim:

1. A medical device for treating a patient suffering from glaucoma where intraocular fluid collects in the intraocular chamber of the eye of a patient elevating the intraocular pressure, including a valve having a body member holding a pair of overlying elastic membranes in tension to form therebetween a chamber, said membranes providing an elongated, slit-like opening therebetween, which is normally in a closed position and opens when the pressure in the chamber exceeds a predetermined pressure and returns to the closed position when the pressure in the chamber is below said predetermined pressure, and an inlet tube in communication with and connected to the chamber at a point remote from the opening, a primary distribution plate connected to the valve and adapted to be placed in one selected ocular quadrant of the eye, said primary distribution plate having a raised perimeter with at least one opening in said perimeter, a secondary distribution plate adapted to be placed in another selected ocular quadrant of the eye and having a raised perimeter with at least one opening in said perimeter, at least one pair of solid plugs, each one inserted into an opening in the perimeters of the primary and secondary distribution plates, said solid plugs being removable, at least one pair of secondary plugs, each having a central passageway, said secondary plugs being inserted into the openings in the perimeters of the primary and secondary distribution plates upon the removal of the solid plugs, an connecting tube sized to fit inside the central passageway of the secondary plugs and inserted in said openings with the distance between the primary and secondary distribution plates being adjusted by positioning the secondary plugs along the length of said connecting tube, said connecting tube placing the primary and secondary distribution plates in fluid communication with each other.

2. The medical device of claim 1 where the plugs are made of silicone.

3. The medical device of claim 1 where the distribution plates are essentially oval in shape.

4. The medical device of claim 1 where there are a plurality of secondary distribution plates.

5. The medical device of claim 1 where the primary and secondary distribution plates are curved to conform to the shape of the surface of eye.

6. The medical device of claim 1 where the valve is a one-way flow device.

7. The medical device of claim 1 where the secondary plugs have a diameter slightly greater than the diameter of the openings, said secondary plugs being placed in tension prior to being inserted into the opening to elongate said plugs slightly so that upon with the release of the tension the plugs fit snug within the opening to hold the connecting tube firmly.

8. The medical device of claim 1 where the raised perimeters of the primary and secondary plates each have a predetermined thickness and the secondary plugs each have a body member with a stop element at each end thereof, the distance between the stops elements being slightly less than the thickness of the raised perimeters so that the body members are elongated when the secondary plugs are inserted into the openings.

9. A medical device, including a one-way flow valve in communication with fluid to be drained, a primary distribution plate affixed to the valve, said primary distribution plate having a raised perimeter with at least one opening in the perimeter, a secondary distribution plate having a raised perimeter with at least one opening in the perimeter, at least one pair of plugs, each having a central passageway, one plug being inserted into the openings in the perimeter of the primary distribution plate and the other being inserted into the openings in the perimeter of the secondary distribution plate, a connecting tube for placing the primary and secondary distribution plates in fluid communication with each other and sized to fit inside the central passageway of the plugs, with said connecting tube having opposed ends, each end inserted to a passageway in said plugs, with the distance between plugs being adjusted by sliding the plugs along the length of said connecting tube.

10. A method for treating glaucoma by draining fluid from the intraocular chamber of a patient's eye, including the steps of (a) providing a medical device including a one-way flow valve attached to a primary distribution plate, said valve having an inlet tube which is placed in communication with the intraocular chamber of the eye so that the fluid drains from the intraocular chamber onto the primary distribution plate under the control of the valve, (b) providing a secondary distribution plate, said primary and secondary distribution plates each having raised perimeters with openings therein adapted to receive plugs, said openings each having diameters of predetermined dimensions, (c) positioning the one-way flow valve with the attached primary distribution plate in a selected ocular quadrant of the eye and providing an connecting tube having opposed ends at which are elastic plugs which each have a passageway therein that receives the connecting tube, (d) positioning the secondary distribution plates in another selected ocular quadrant of the eye and placing the primary distribution plate and the secondary distribution plate in communication with each other through the connecting tube by inserting one plug into the opening in the perimeter of the primary distribution plate and inserting the other plug into the opening in the perimeter of the secondary distribution plate, with the distance between the plates being adjusted to approximately equal the distance between the primary and secondary plates, each plug having a diameter slightly greater than the diameter of the opening in which it is inserted, (h) stretching the plugs prior to inserting them into the openings and then releasing the plugs after insertion so that the plugs fit snugly in the openings and the diameter of the passageways in the plugs is reduced slightly to hold the connecting tube snugly but not to prevent fluid flow.

11. The method of claim 10 where there are additional secondary distribution plates employed.

12. The method of claim 10 where the secondary plugs have a diameter slightly greater than the diameter of the openings, said secondary plugs being placed in tension prior to being inserted into the opening to elongate said plugs slightly so that upon with the release of the tension the plugs fit snug within the opening to hold the connecting tube firmly.

13. The method of claim 10 where the raised perimeters of the primary ands secondary plates each have a predetermined thickness and the secondary plugs each have a body member with a stop element at each end thereof, the distance between the stops elements being slightly less than the thickness of the raised perimeters so that the body members are elongated when the secondary plugs are inserted into the openings.

14. The method of claim 10 where the connecting tube is positioned above eye muscles.

15. The method of claim 10 where the connecting tube is positioned below eye muscles.

16. The method of claim 10 where the plugs are located in the perimeters of the plates so that they may be selectively removed for either right or left hand access.

* * * * *